: US 12,265,081 B2
(45) Date of Patent: Apr. 1, 2025

(54) FILOVIRUS ANTIBODIES AND METHODS

(71) Applicants: UNM RAINFOREST INNOVATIONS, Albuquerque, NM (US); Ravi Durvasula, Albuquerque, NM (US); Steven Bradfute, Albuquerque, NM (US); Adinarayana Kunamneni, Albuquerque, NM (US)

(72) Inventors: Ravi Durvasula, Albuquerque, NM (US); Steven Bradfute, Albuquerque, NM (US); Adinarayana Kunamneni, Albuquerque, NM (US)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 807 days.

(21) Appl. No.: 17/436,782

(22) PCT Filed: Mar. 4, 2020

(86) PCT No.: PCT/US2020/020982
§ 371 (c)(1),
(2) Date: Sep. 7, 2021

(87) PCT Pub. No.: WO2020/185464
PCT Pub. Date: Sep. 17, 2020

(65) Prior Publication Data
US 2023/0212268 A1    Jul. 6, 2023

Related U.S. Application Data

(60) Provisional application No. 62/815,435, filed on Mar. 8, 2019, provisional application No. 62/890,788, filed on Aug. 23, 2019.

(51) Int. Cl.
*G01N 33/569*    (2006.01)
*A61P 31/14*    (2006.01)
*C07K 16/10*    (2006.01)

(52) U.S. Cl.
CPC ........ *G01N 33/56983* (2013.01); *A61P 31/14* (2018.01); *C07K 16/10* (2013.01); *C07K 16/1018* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2013/0323243 A1* | 12/2013 | Kaplan | G01N 33/6854 435/5 |
| 2017/0158753 A1* | 6/2017 | Aman | G01N 33/56983 |
| 2017/0182163 A1* | 6/2017 | Lai | A61K 39/42 |
| 2018/0030118 A1* | 2/2018 | Johnstone | A61P 31/12 |
| 2018/0141999 A1* | 5/2018 | Chandran | C07K 16/468 |
| 2018/0237502 A1* | 8/2018 | Aman | A61P 31/14 |
| 2019/0185547 A1* | 6/2019 | Lai | C07K 16/24 |

OTHER PUBLICATIONS

Kunamneni, A., Clarke, E. C., Ye, C., Bradfute, S. B., & Durvasula, R. Generation and Selection of a Panel of Pan-Filovirus Single-Chain Antibodies using Cell-Free Ribosome Display. bioRxiv, pre-print, Epub May 21, 2018, pp. 1-32. (Year: 2018).*
International Patent Application No. PCT/US2020/020982, filed Mar. 4, 2020; International Search Report and Written Opinion, issued Jun. 25, 2020; 7 pages.
International Patent Application No. PCT/US2020/020982, filed Mar. 4, 2020; International Preliminary Report on Patentability, issued Aug. 25, 2021; 6 pages.
Kunamneni "Generation and Selection of a Panel of Pan-Filovirus Single-Chain Antibodies using Cell-Free Ribosome Display" 2019, *Am. J. Trop. Med. Hyg.*, vol. 101, No. 1, pp. 198-206.

* cited by examiner

*Primary Examiner* — Janet L Andres
*Assistant Examiner* — Carey Alexander Stuart
(74) *Attorney, Agent, or Firm* — Mueting Raasch Group

(57) ABSTRACT

An antibody that binds to a filovirus glycoprotein generally includes include a complementarity determining region (CDR) of any one of SEQ ID NO:27-36 or a combination of such CDRs. The antibody may be used in to detect filovirus in a biological sample obtained from a subject. The antibody also may be formulated into a pharmaceutical composition for administering to a subject having, or at risk of having, a filovirus infection.

16 Claims, 14 Drawing Sheets

Specification includes a Sequence Listing.

EBOV-specific $V_H/K$

FILOVIRUS ANTIBODIES AND METHODS

CROSS-REFERENCE TO RELATED APPLICATION

This application is the § 371 U.S. National Stage of International Application No. PCT/US2020/020982, filed Mar. 4, 2020, which claims the benefit of U.S. Provisional Patent Application No. 62/815,435, filed Mar. 8, 2019, and U.S. Provisional Patent Application No. 62/890,788, filed Aug. 23, 2019, each of which is incorporated herein by reference in its entirety.

GOVERNMENT FUNDING

This invention was made with government support under HDTRA1-15-1-0061 awarded by the Defense Threat Reduction Agency. The government has certain rights in the invention.

SEQUENCE LISTING

This application contains a Sequence Listing electronically submitted to the United States Patent and Trademark Office via EFS-Web as an ASCII text file entitled "0310000108WO01_ST25.txt" having a size of 32 bytes and created on Mar. 2, 2020. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

SUMMARY

This disclosure describes, in one aspect, an antibody that binds to filovirus glycoproteins. In some embodiments, the antibody can include a complementarity determining region (CDR) of any one of SEQ ID NO:27-36 or a combination of such CDRs.

In some embodiments, the antibody can be an antibody fragment.

In some embodiments, the antibody binds to at least one of: EBOV glycoprotein, SUDV glycoprotein, RESTV glycoprotein, BDBV glycoprotein, MARV glycoprotein, or TAFV glycoprotein. In some embodiments, the antibody binds to EBOV glycoprotein, SUDV glycoprotein, RESTV glycoprotein, BDBV glycoprotein, MARV glycoprotein, and TAFV glycoprotein.

In another aspect, this disclosure describes a method of detecting a filovirus in a biological sample obtained from a subject. Generally, the method includes obtaining the biological sample from the subject, contacting an embodiments of the antibody summarized above with the biological sample under conditions effective to allow the antibody to bind to filovirus in the sample, thereby forming an antibody:target complex and detecting the antibody:target complex.

In some embodiments, the filovirus is an ebolavirus. In other embodiments, the filovirus is a marburgvirus.

In some embodiments, the antibody:target complex is detected by performing an enzyme-linked immunoassay (ELISA).

In some embodiments, the antibody:target complex is detected by performing a Western blot analysis.

In some embodiments, the antibody:target complex is detected by performing an immunofluorescence assay.

In another aspect, this disclosure describes a method of treating a subject having, or at risk of having, a filovirus infection. Generally, the method includes administering to the subject an effective amount of a pharmaceutical composition that includes any embodiment of the antibody summarized above.

In some embodiments, the pharmaceutical composition is administered before the subject exhibits a symptom or clinical sign of having a filovirus infection.

In some embodiments, the pharmaceutical composition is administered after the subject exhibits a symptom or clinical sign of having a filovirus infection.

In some embodiments, the filovirus is an ebolavirus. In other embodiments, the filovirus is a marburgvirus.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Figure 5A:
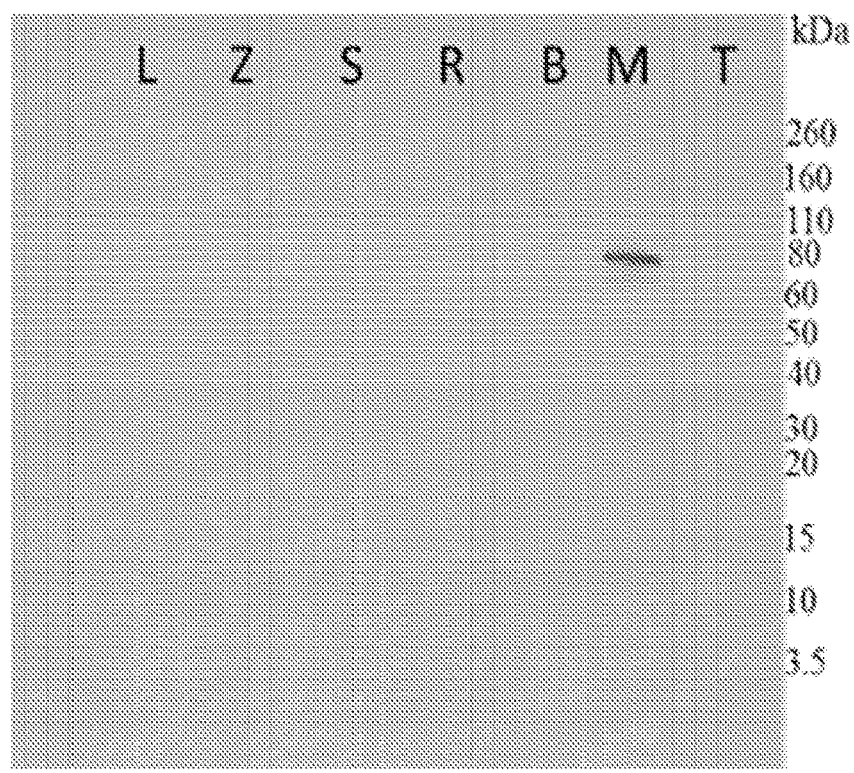
Figure 5B:
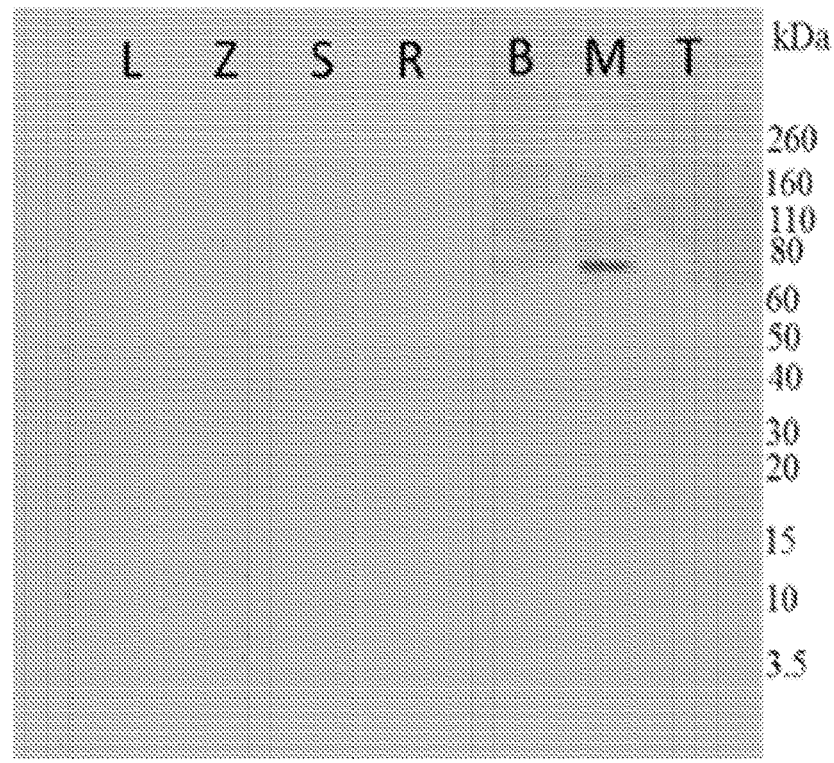

FIG. 5. Denaturation eliminates binding of scFv4-2 and scFv22-1 for the ebolavirus glycoproteins. (A) The purified proteins of LLOV (L), EBOV (Z), SUDV (S), RESTV (R), BDBV (B), MARV (M), and TAFV (T) glycoproteins without transmembrane (TM) domain were probed with soluble scFv 4-2. (B) The purified proteins of LLOV (L), EBOV (Z), SUDV (S), RESTV (R), BDBV (B), MARV (M), and TAFV (T) glycoproteins without TM were probed with soluble scFv 22-1.

Figure 6A:
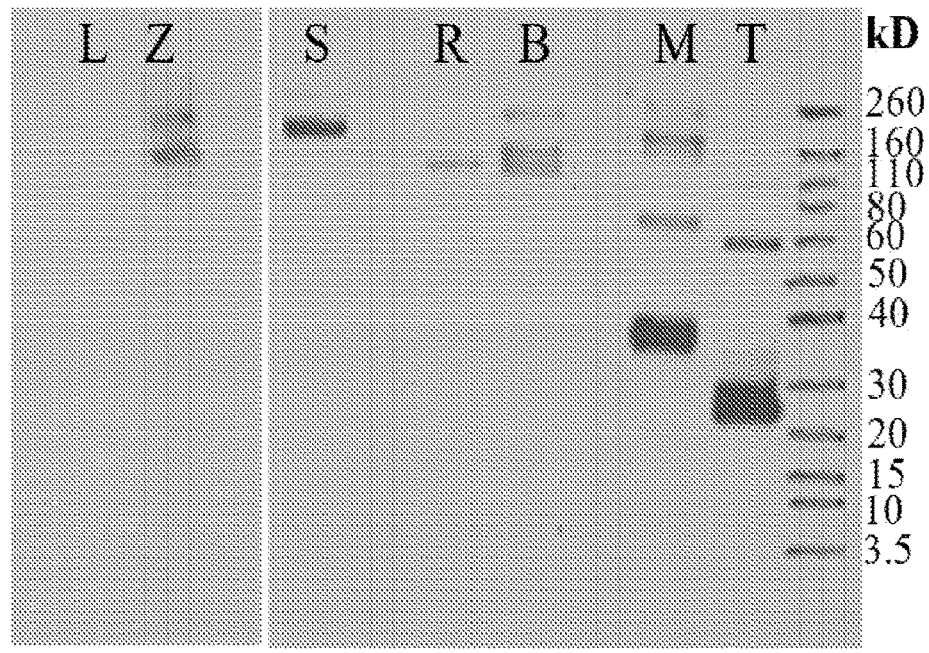
Figure 6B:
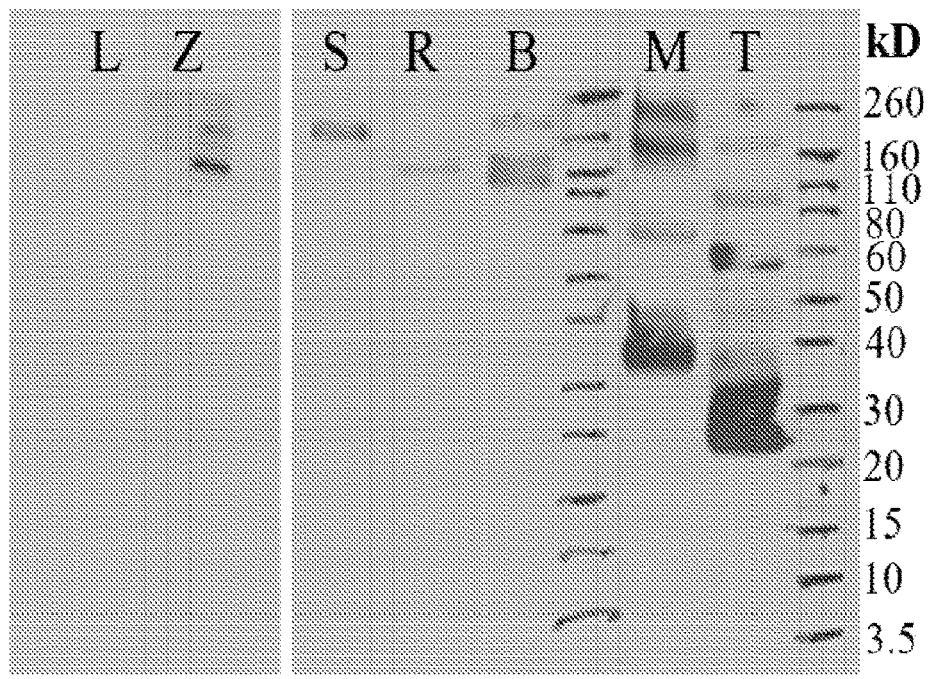

FIG. 6. Immunoprecipitation of filovirus glycoproteins by scFv4-2 and scFv22-1. (A) The lysates of LLOV (L), EBOV (Z), SUDV (S), RESTV (R), BDBV (B), MARV (M), and TAFV (T)-infected 293T cells were immunoprecipitated with soluble scFv4-2 followed by SDS-PAGE analysis and Western blot. (B) The lysates of LLOV (L), EBOV (Z), SUDV (S), RESTV (R), BDBV (B), MARV (M), and TAFV (T)-infected 293T cells were immunoprecipitated with soluble scFv22-1 followed by SDS-PAGE analysis and Western blot.

Figure 7:
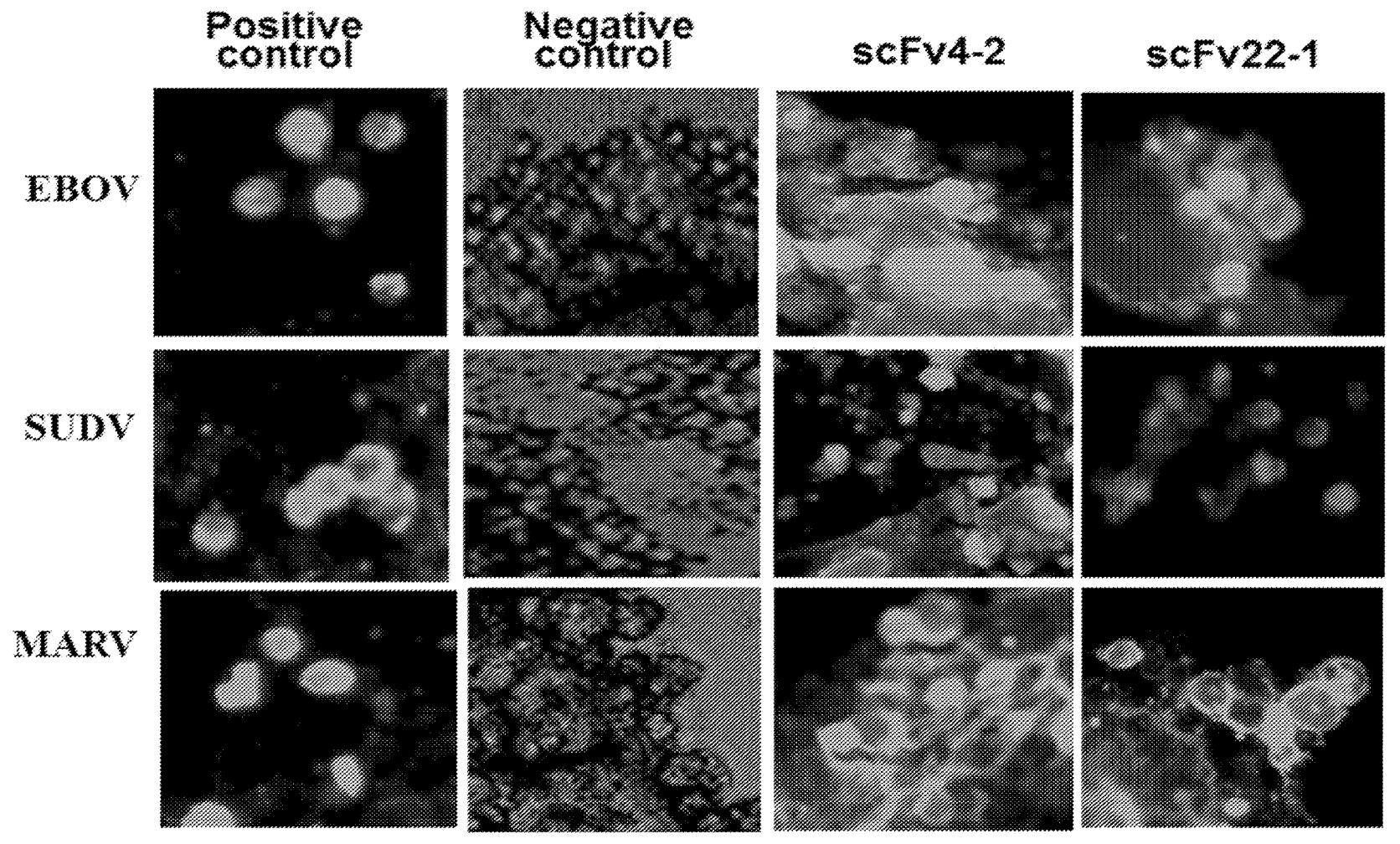

FIG. 7. scFv4-2, scFv22-1, and positive controls recognize the natural forms of $GP1,2_{ZEBOV}$, $GP1,2_{SUDV}$, and $GP1,2_{MARV}$ by IFA.

Figure 8:
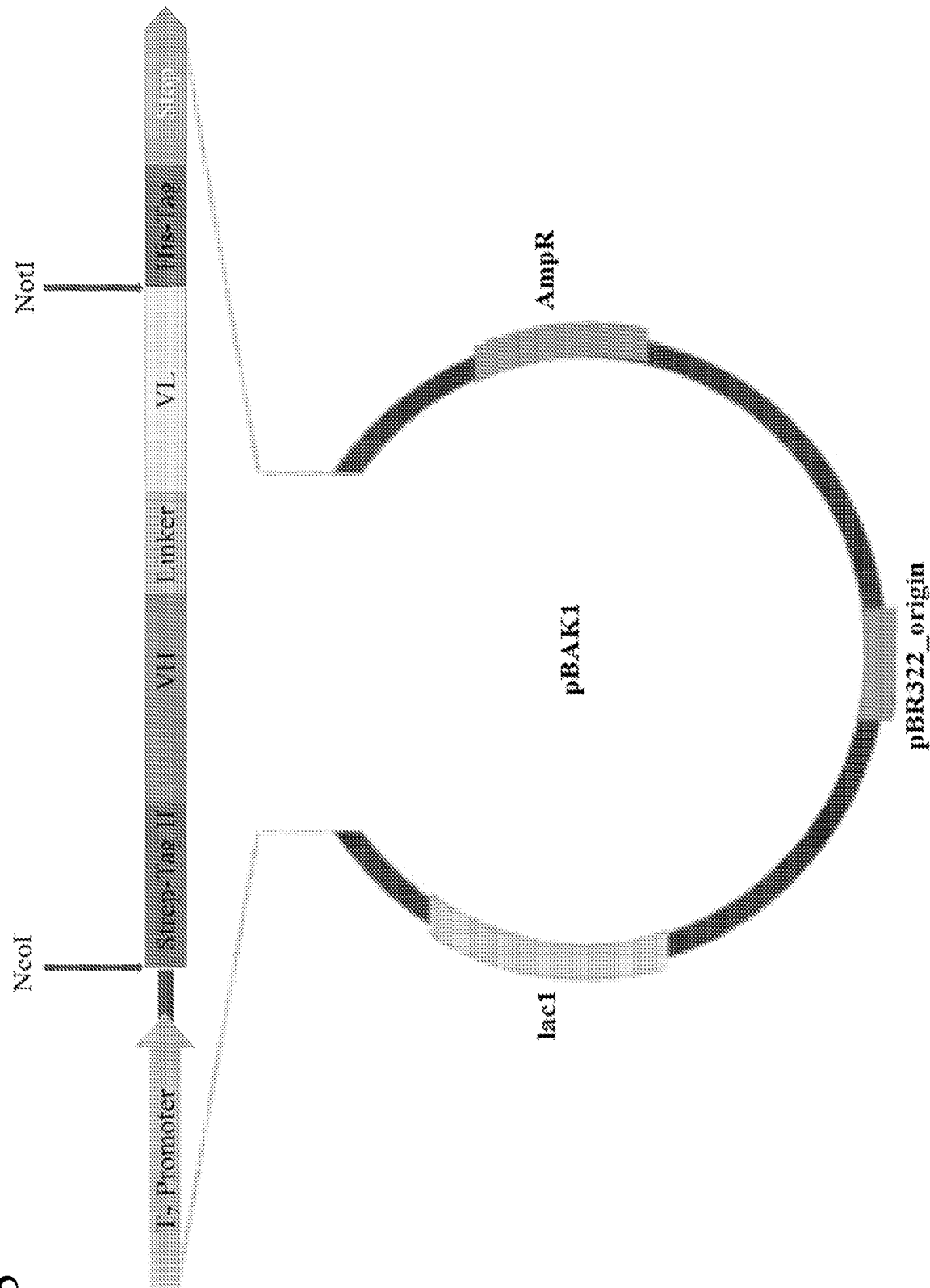

FIG. 8. Schematic diagram of the pBAK1 (anti-EbovGP-his-ScFv) expression vector. The position of the enzymatic cleavage is indicated by the vertical arrows. The gene encoding anti-EbovGP-his-ScFv protein was inserted into the pBAK1 vector under the control of the T7lac promoter, in frame with a strep tag II.

Figure 9:
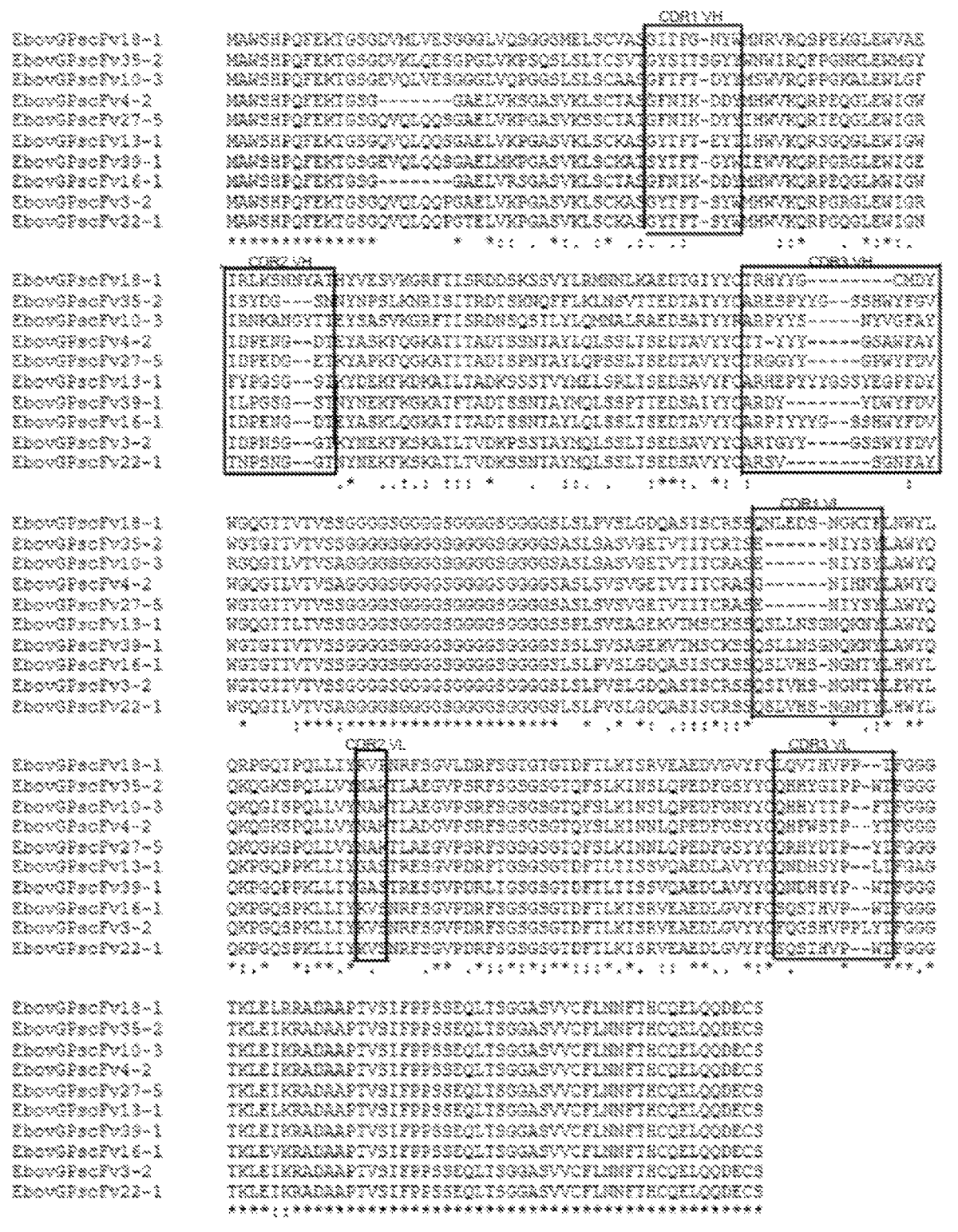

FIG. 9. Alignment of the derived amino acid sequences (SEQ ID NOs:27-36) of the randomly chosen scFvs from linked antibody library and complementary determining regions (CDRs). Framework regions (FRs) and CDRs are determined by the IMGT information system. Diversity was found predominantly in the CDR regions, which are boxed and labeled. A normal 20 amino acid linker $[(G_4S)_4]$ joins the $V_H$ and $V_L$ chains. Symbols in the alignment are as follows: (*) indicates where there is a conserved amino acid; (:) indicates an amino acid position with conserved similarity; (.) indicates a semi-conserved amino substitution has occurred; (-) indicates spaces introduced to optimize the alignment. EbovGPscFv18-1: SEQ ID NO:27; EbovGPscFv35-2: SEQ ID NO:28; EbovGPscFv10-3: SEQ ID NO:29; EbovGPscFv4-2: SEQ ID NO:30; EbovGPscFv27-5: SEQ ID NO:31; EbovGPscFv13-1: SEQ ID NO:32; EbovGPscFv39-1: SEQ ID NO:33; EbovGPscFv16-1: SEQ ID NO:34; EbovGPscFv3-2: SEQ ID NO:35; EbovGPscFv22-1: SEQ ID NO:36.

Figure 10A:
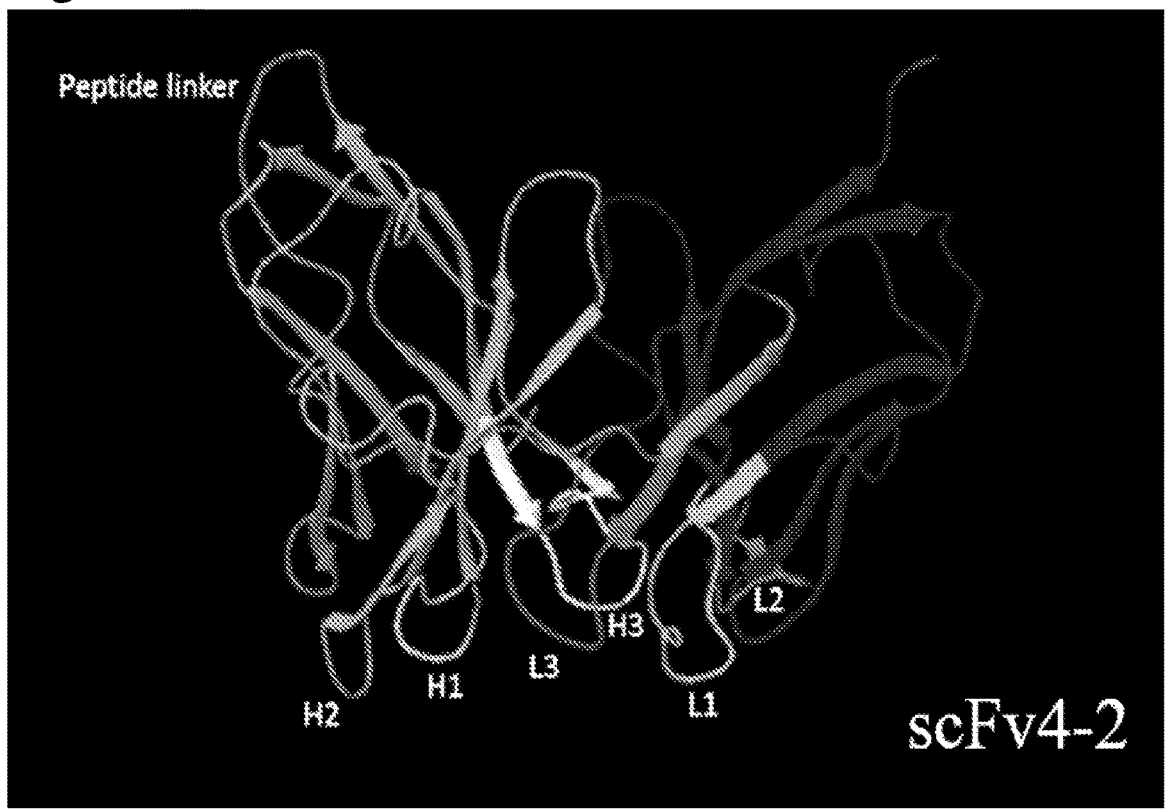
Figure 10B:
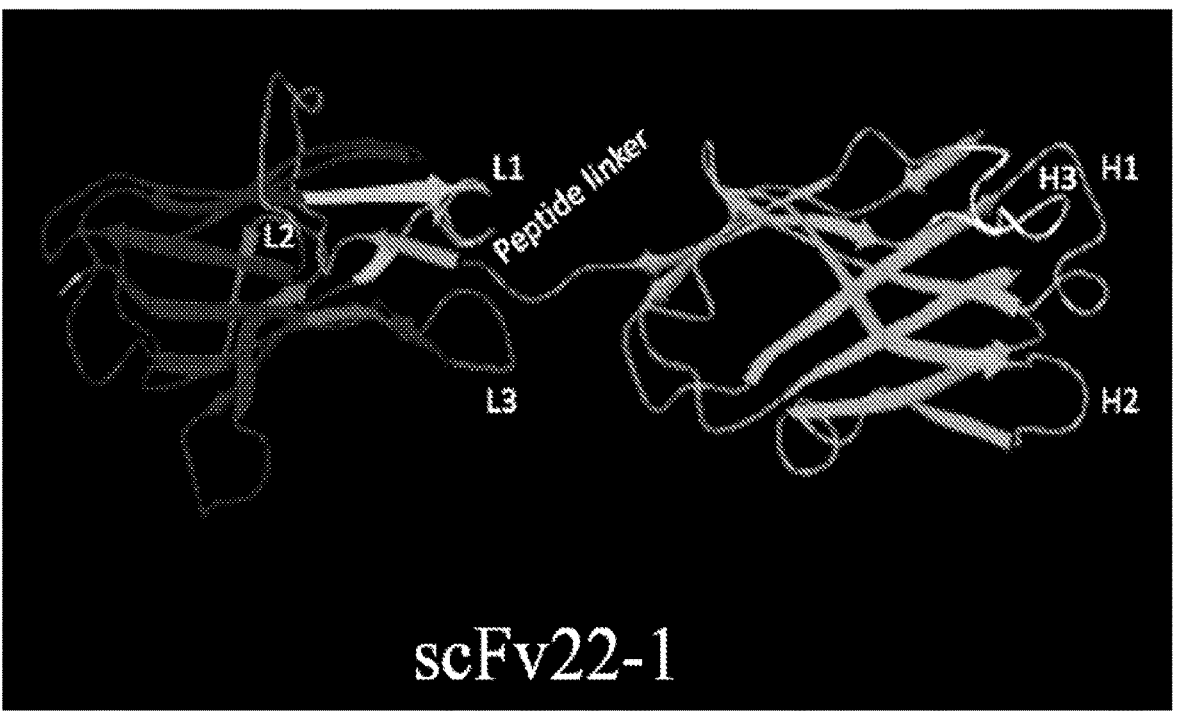

FIG. 10. Predicted Ribbon representation of anti-ZEBOV scFv antibody molecules in 3D mode. (A) scFv4-2. (B) scFv22-1.

DETAILED DESCRIPTION OF ILLUSTRATIVE EMBODIMENTS

This disclosure describes antibodies that bind to filovirus glycoproteins, cell-free ribosomal display methods for rapidly generating such antibodies, and methods of using such antibodies. In one aspect, the antibodies may be used to identify a subject as having been exposed to a filovirus such as, for example, an ebolavirus or a marburgvirus.

Filoviruses, which include ebolaviruses and marburgvirus, can cause outbreaks of highly lethal hemorrhagic fever, which causes significant morbidity and mortality in humans, with human fatality rates reaching 90% during some outbreaks. Since early symptoms of filovirus infection mimic more common diseases, there is a strong unmet public health and biodefense need for rapid, broad-spectrum detection of filovirus.

This disclosure describes generating a panel of mouse single-chain Fv-antibodies (scFvs) to filovirus glycoproteins (GPs) using cell-free ribosome display. The svFvs were generated using a rapid, cell-free ribosomal display system to isolate a panel of scFvs that can bind the glycoprotein (GP) of EBOV, SUDV, RESTV, BDBV, TAFV, and MARV. The resulting scFvs have been characterized in a range of in vitro assays, including cross-reactivity profiles to all known filovirus species. Two scFvs (scFv4-2 and scFv22-1) were able to detect all known species of the genera Ebolavirus and Marburgvirus. The scFvs described herein can detect a broad set of filovirus glycoproteins.

Anti-ZEBOVGP scFv Antibodies Generated from Cell-Free Ribosomal Display

To determine whether ribosomal display is suitable generating antibodies against filoviruses, mice were vaccinated with virus-like particles (VLPs) containing EBOV VP40 and glycoprotein.

Figure 1:
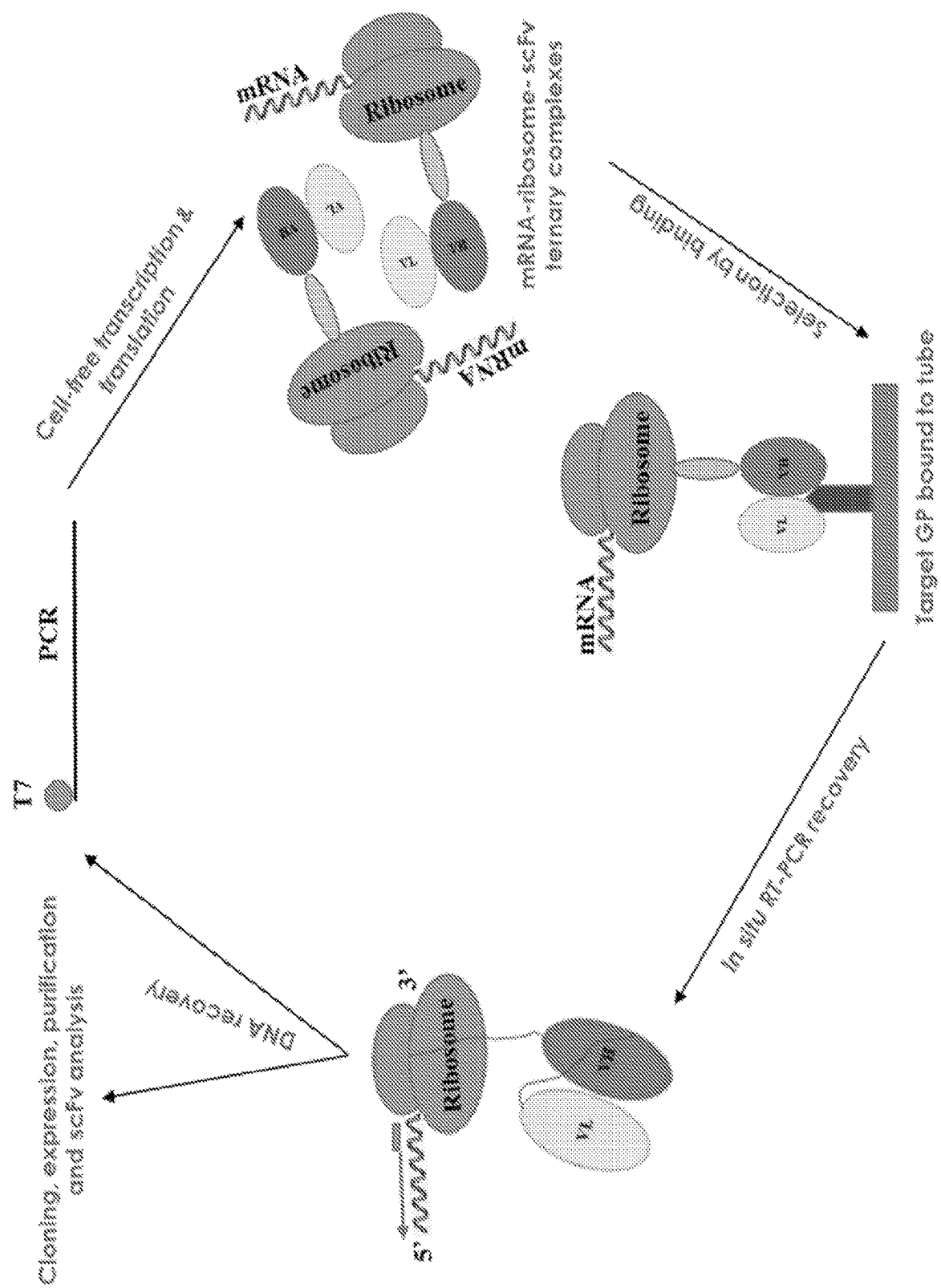
FIG. 1. Graphical summary of cell-free ribosomal display used to generate scFVs. scFvs were generated using mice immunized with filovirus VLPs.
Figure 2A:
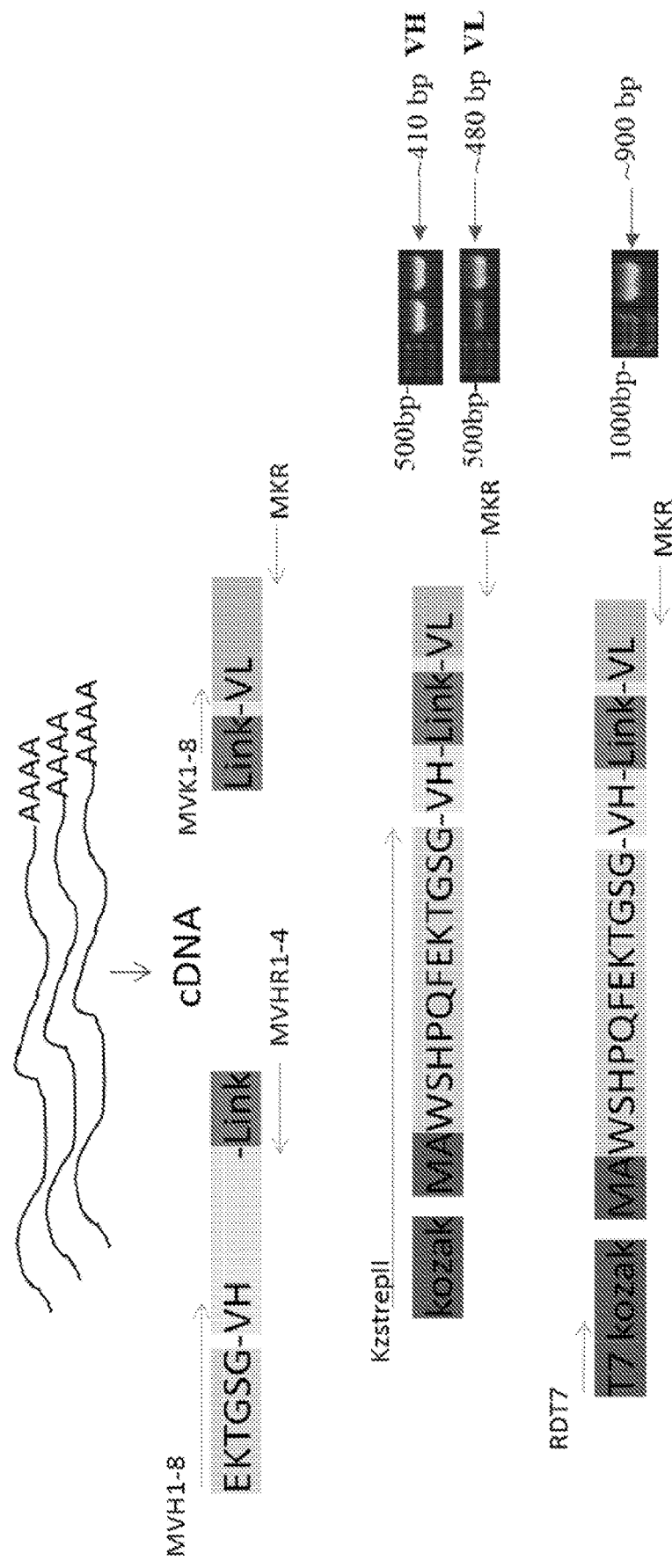
FIG. 2. Preparation and recovery of scFvs. (A) Schematic representation of making scFv library from mouse spleen. MVH1-8 contains amoino acids 9-14 of SEQ ID NO:27; KzstrepII and RDT7 contain amino acids 1-14 of SEQ ID NO: 27. (B) Schematic illustration of stalled ARM complex and position of primers used for RT-PCR recovery in the first cycle of ribosome display. T7 is the 5' primer and MKR is the 3' primer. (C) Analysis of RT-PCR recovery of $V_H$/K cDNA in the first cycle. VH/K complexes were bound to EBOV glycoprotein coated to the PCR tube through the first cycle of selection and recovery.

For ribosome display, scFv antibody libraries were generated by joining immunoglobulin $V_H$ and $V_L$ regions using a 20-amino-acid flexible linker $[(G_4S)_4]$, using RNA isolated from the spleen of an immunized mouse (FIG. 1, FIG. 2). cDNA was synthesized using a single consensus primer and then pooled and directly used as a template for PCR amplification of the $V_H$ and $V_L$ chain gene fragments. Briefly, the gene fragments were pooled in one reaction tube together with primers that contain overlapping linker sequences that allow the $V_H$ and $V_L$ gene segments to be assembled by overlap extension to form strep tag-conjugated scFvs (FIG. 2). The amplified PCR product was the expected size of about 900 bp. The final DNA template encoding the library flanked by a T7 site was used in an in vitro ribosome display with a single selection step with recombinant EBOV glycoprotein as outlined in FIG. 1.

Figures 2B, 2C:
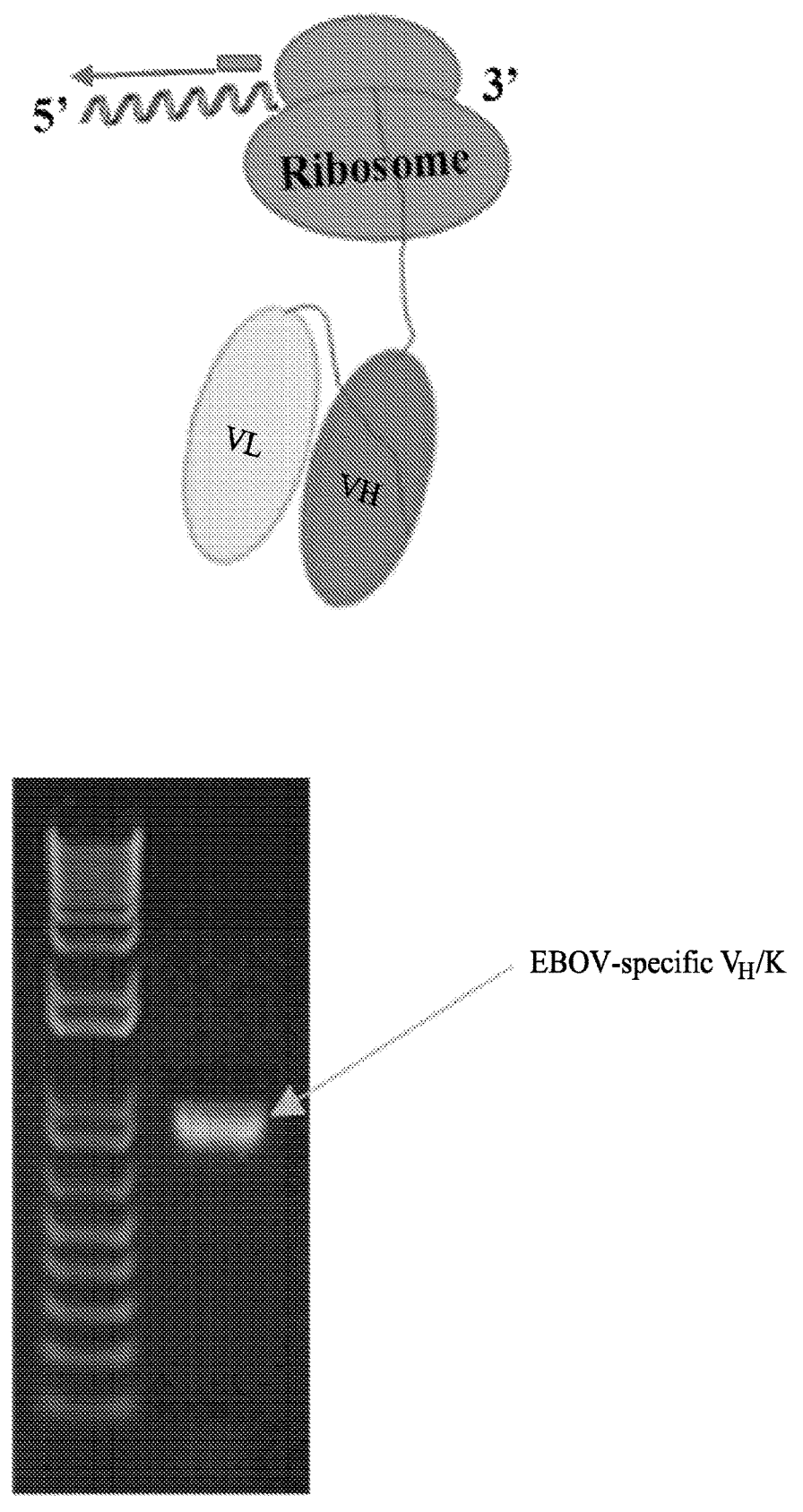

After selection, the mRNA was recovered as DNA from the bound ternary complexes by in situ RT-PCR (FIG. 2B, 2C). The cDNAs encoding anti-EBOV-glycoprotein scFvs and selected from the first round of PCR were cloned into pGEM-T vector and transformed into XL1-Blue competent cells. About 50 colonies were sequenced and 10 clones were subjected to sequence alignment analysis using Clustal Omega. The aligned amino acid sequences of ten clones from library are shown in FIG. 9.

The aligned amino acid sequences revealed three complementary determining regions (CDRs) and four framework regions (FRs) in each of the heavy chain ($V_H$) and light chain ($V_L$) fragment, which were linked by a 20-amino-acid $[(G_4S)_4]$ linker. Significant diversity in the $V_H$ and $V_L$ chains was observed, especially in the CDRs (FIG. 9, boxes). Variability was also noted in the framework regions. No two clones had identical $V_H$ or $V_L$ fragments.

The framework regions (FRs) and CDRs were determined by the IMGT information system (Giudicelli et al., 2004, Nucleic Acids Res 32(Web Server issue):W435-440). The length of CDRs was variable: CDR1 $V_H$ had an average length of eight amino acid residues; CDR2 $V_H$ had an average length of eight residues; CDR3 $V_H$ ranged from 10 to 18 amino acid residues, with an average length of 13 residues; CDR1 $V_L$ with an average length of nine residues; CDR2 $V_L$ has a length of three amino acids, and the most common length of CDR3 $V_L$ was nine amino acid residues.

Figure 3A:
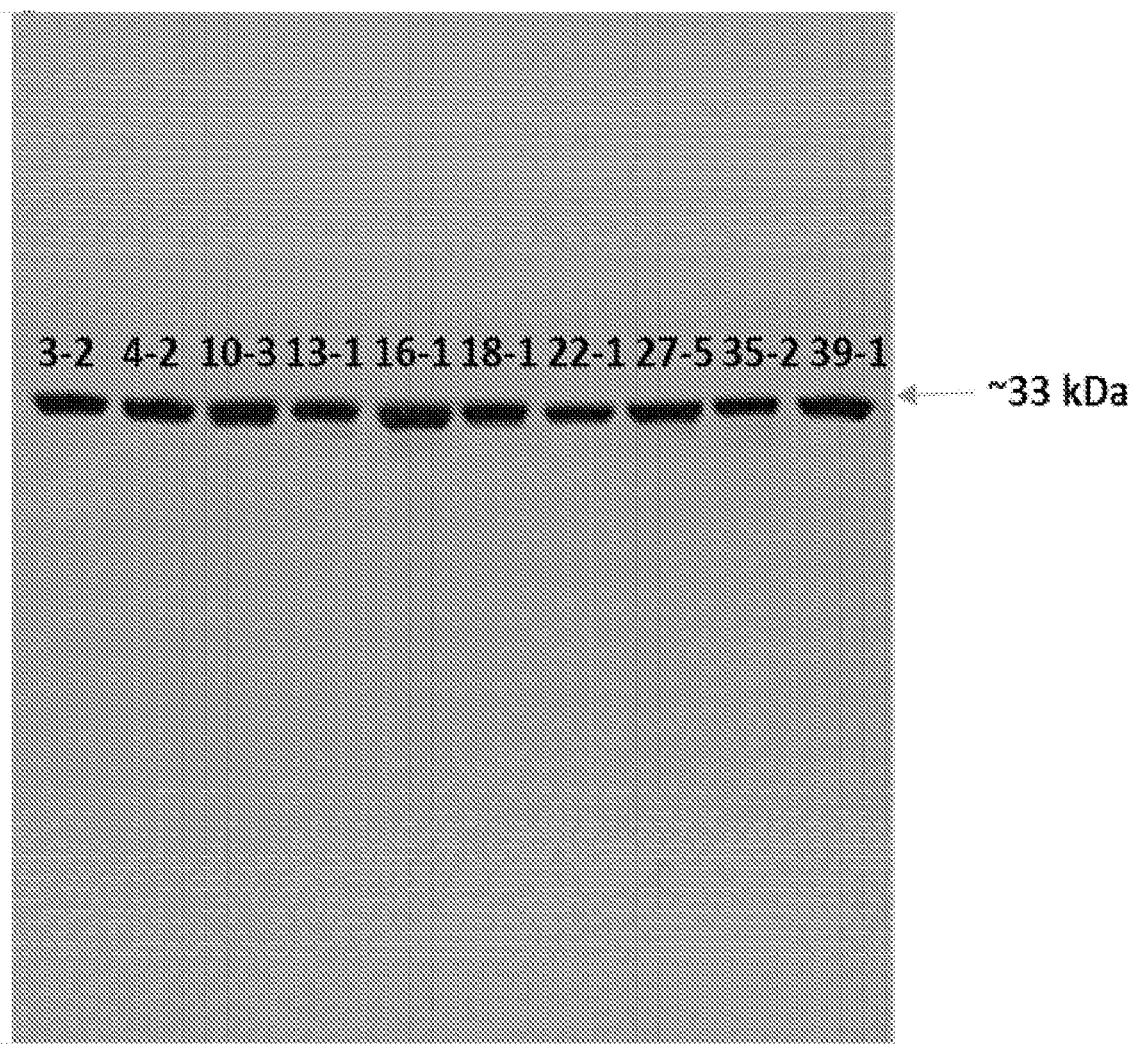
FIG. 3. Characterization of scFvs. (A) Western blot of purified scFvs (3-2, 4-2, 10-3, 13-1, 16-1, 18-1 22-1, 27-5, 35-2 and 39-1). (B) ELISA results for purified novel anti-EBOV scFv4-2 generated by ribosome display. (C) ELISA results for purified novel anti-EBOV scFv22-1 generated by ribosome display. Commercial monoclonal [(EBOV:mouse anti-EBOV antibody 6D8 (IBT Bioservices, Inc., Rockville, MD); SUDV:mouse anti-SUDV ebola virus antibody (clone 6D11, BEI Resources, Manassas, VA)] and polyclonal [(RESTV:rabbit anti-RESTV GP (IBT Bioservices, Rockville, MD); BDBV:rabbit anti-BDBV GP (IBT Bioservices, Rockville, MD); MARV:rabbit anti-MARV GP (IBT Bioservices, Rockville, MD); TAFV:rabbit anti-TAFV GP (Alpha Diagnostic International, Inc., San Antonio, TX)] antibodies as positive controls, and an scFv negative control [(mouse anti-PilB scFv21 antibody (unpublished data)].

Prokaryotic expression of the selected scFvs was performed in Rosetta gami B(DE3) E. coli (Novagen, Inc., Madison, WI) with the expression vector pBAK1 (Markiv et al., 2011, *J Immunol Methods* 364(1-2):40-49), which is known to increase the solubility of the expressed proteins. After the scFv clones were expressed, samples were harvested, lysed, purified, and fractions were analyzed by SDS-PAGE followed by Western blot. The purified protein gave a prominent band of about 33 kDa (FIG. 3A).

Specificity, Cross-Reactivity and Affinity of Glycoprotein-Specific scFvs

Figure 3B:
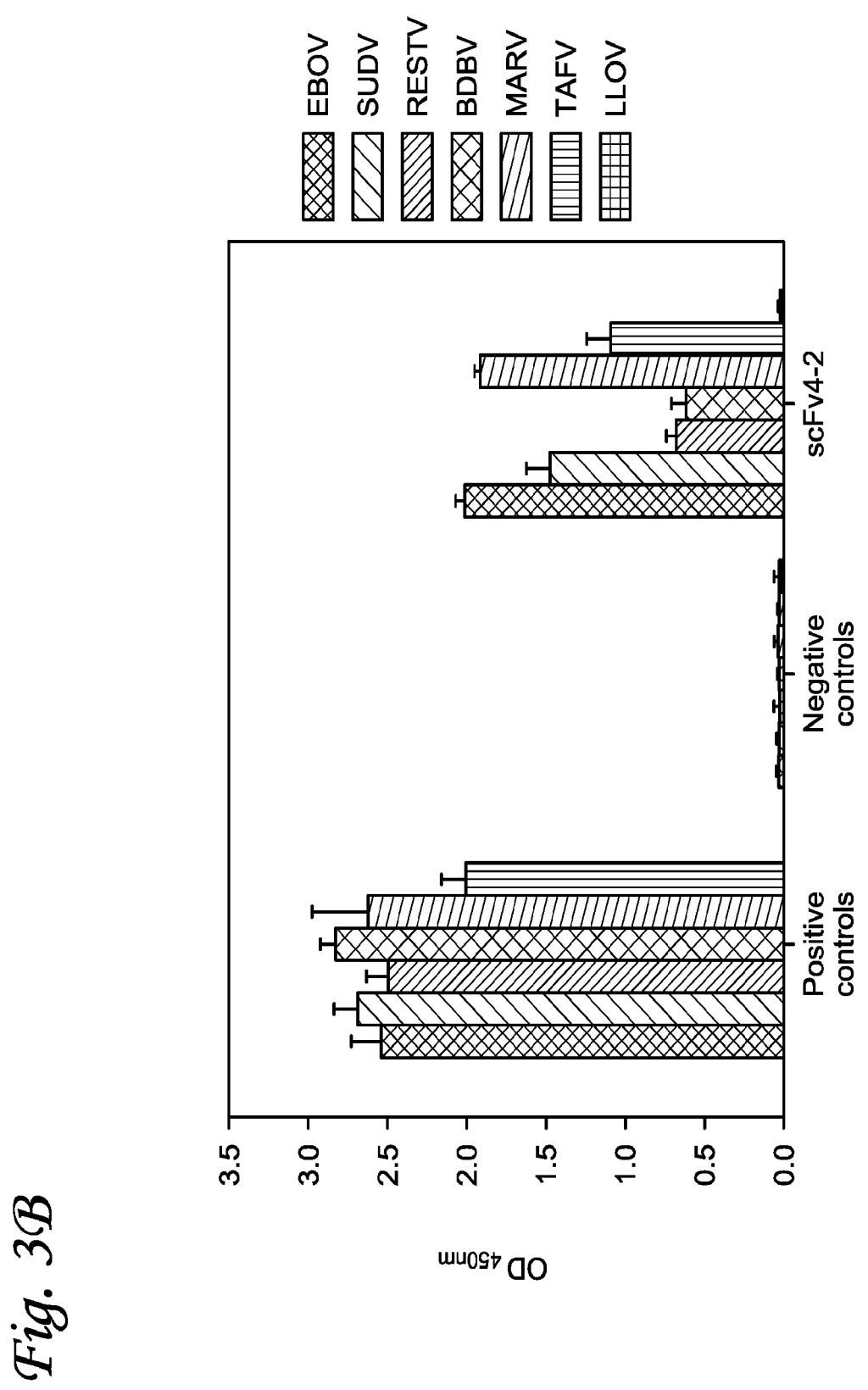
Figure 3C:
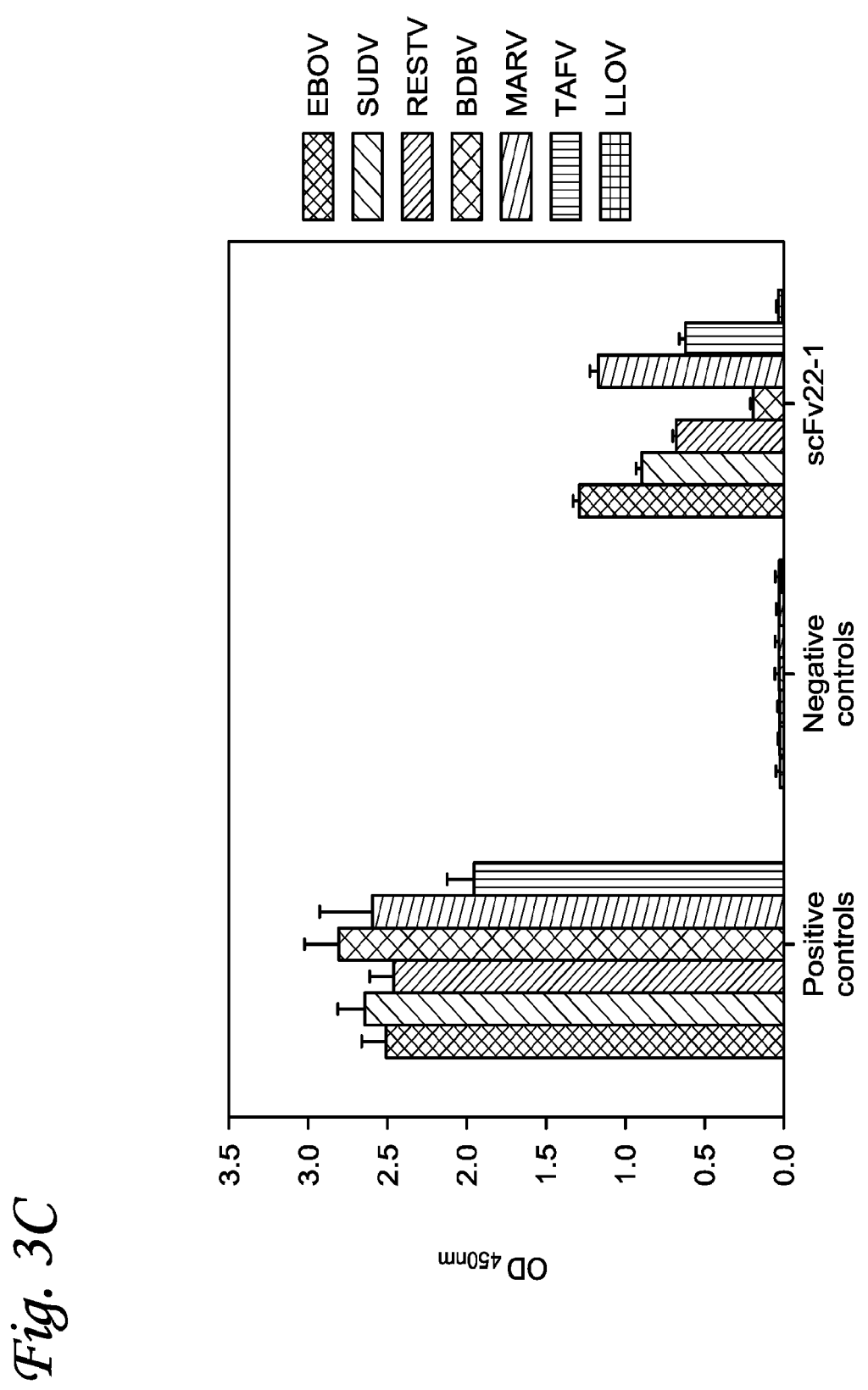

The scFvs were screened in ELISA binding assays for their specificity and cross-reactivity with recombinant glycoproteins of the other known filoviruses in the genus Ebolavirus (SUDV, TAFV, BDBV, and RESTV) and Marburgvirus (MARV). Several different profiles for the cross-reactivities of these antibodies were found. Two scFvs, scFv4-2 (FIG. 3B) and scFv22-1 (FIG. 3C), reacted strongly with all tested glycoproteins of Ebolavirus and Marburgvirus species. Six scFvs (scFv3-2, scFv13-1, 16-1, scFv18-1, scFv35-2, and scFv35-1) bound weakly to glycoproteins of some viruses in addition to EBOV, scFv3-2 reacted only to TAFV and MARV, and scFv27-5 didn't react with any glycoproteins. Importantly, these different reactivity profiles enable one to distinguish the known Ebolavirus species by using scFv4-2 and scFv22-1, as shown in FIG. 3B and FIG. 3C. Representative scFvs for each cross-reactivity profile that showed the highest OD values were selected for dose response relationship studies based on the overlap of common motifs.

Figure 4A:
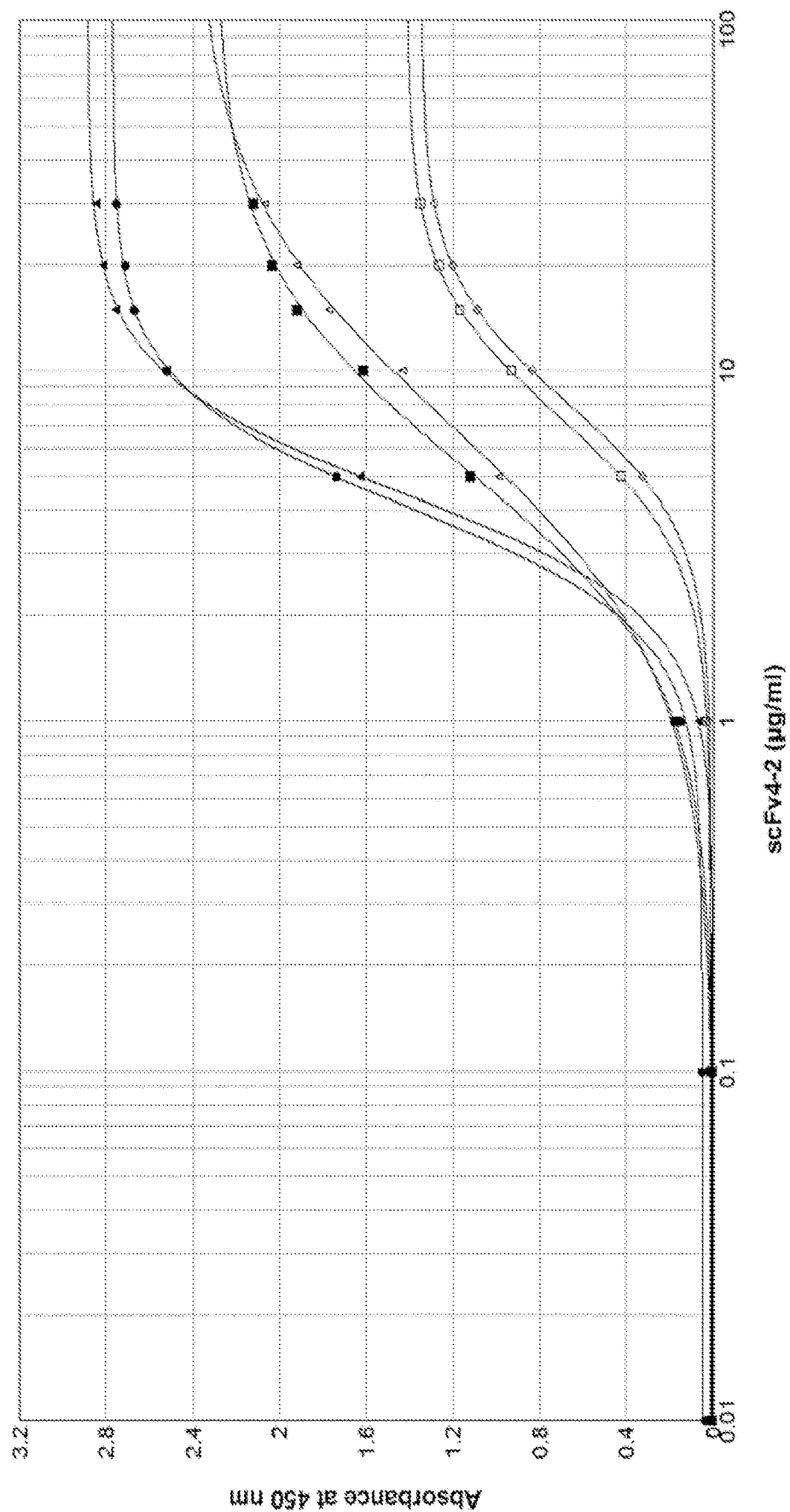
FIG. 4. Reactivity of mouse ZEBOV glycoprotein scFvs to filovirus glycoproteins and dose response binding of the indicated antibodies to glycoproteins of ZEBOV (●), SUDV (■), MARV (▲), BDBV (◊), RESV (□), and TAFV (Δ). (A) scFv4-2. The $EC_{50}$ values (in micrograms per milliliter) for binding of scFv4-2: ZEBOV, 4.094; SUDV, 5.298; MARV, 4.506; BDBV, 8.185; RESV, 7.441; and TAFV, 6.948. (B) scFv22-1. The $EC_{50}$ values (in micrograms per milliliter) for binding of scFv22-1: ZEBOV, 7.356; SUDV, 7.943; MARV, 6.584; BDBV, 10.83; RESV, 8.999; and TAFV, 11.57. Values are optical density at 450 nm (OD450) values from three ELISA experiments performed over the indicated range of antibody concentrations.
Figure 4B:
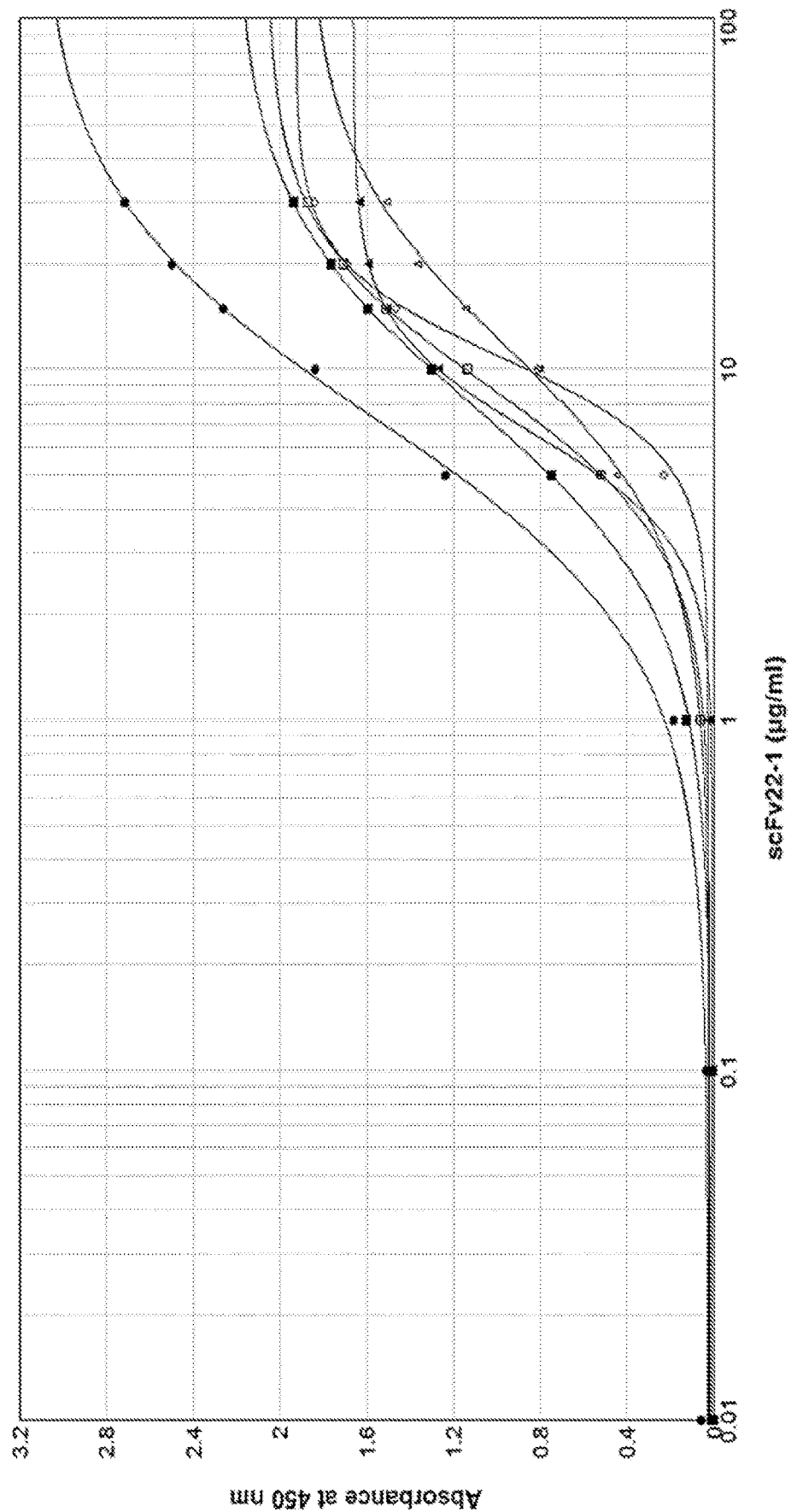

Dose response curves were determined for scFv4-2 and scFv22-1 (FIG. 4A, 4B). Both scFvs bound tightly to all six glycoproteins, with $EC_{50}$s ranging from 4 µg/mL to 12 µg/mL. scFv4-2 and scFv22-1 showed the strongest binding to all six ebolavirus species, with scFv4-2 having an $EC_{50}$ below 9 µg/mL and scFv22-1 having an $EC_{50}$ below 12 µg/mL. scFv4-2 exhibited almost two-fold enhanced binding compared to scFv22-1. Binding constant ($K_D$) determinations were estimated by fitting a dose response curve and the $K_D$ estimates for the scFvs against all six glycoproteins are shown Table 2. The highest affinity scFv was the anti-EBOVGP scFv4-2, which was about two-fold greater towards all six glycoproteins than the anti-EBOVGP scFv22-1.

To assess the ability of the anti-EBOVGP scFvs to recognize the six filovirus glycoproteins in a denatured format, Western blotting was performed on purified glycoproteins. Binding by the anti-EBOVGP scFvs (scFv4-2 and scFv22-1) to ebolavirus glycoproteins was completely lost upon denaturation, while binding to $GP_{MARV}$ was not affected (FIG. 5). The reactivities of these glycoprotein-specific scFvs were further tested by immunoprecipitation analysis (IP) using lysates of filovirus glycoprotein expressed in 293T cells. The anti-EBOVGP scFvs were able to immunoprecipitate filovirus glycoproteins, confirming the ELISA data. (FIG. 6).

An immunofluorescence assay (IFA) was performed to confirm the recognition of scFvs with the proteins of $GP_{EBOV}$, $GP_{SUDV}$, and $GP_{MARV}$ in its natural membrane associated trimeric structure with 293T cells transfected with the $GP_{EBOV}$-expressing plasmid, $GP_{SUDV}$-expressing plasmid, or the $GP_{MARV}$-expressing plasmid (FIG. 7). scFv4-2 and scFv22-1) effectively recognized and stained the $GP_{EBOV}$, $GP_{SUDV}$, and $GP_{MARV}$ expressed in the 293T cells. The staining ability of scFv4-2 was superior to scFv22-1 and these are comparable to the results of positive controls in the immunofluorescence assay.

Thus, this disclosure describes generating a panel of mouse scFvs using cell-free ribosome display with a range of cross-reactivity to five species of ebolaviruses and to marburgvirus. Two of these scFvs can cross-react to all six known pathogenic filoviruses, representing pan-filovirus binding.

Of the 10 anti-EBOV glycoprotein scFvs tested by ELISA, there were two that were highly cross-reactive to all ebolavirus and marburgvirus glycoproteins (FIGS. 3B and 3C), but not LLOV glycoprotein, suggesting that the scFvs are antigen-specific. The cross-reactive scFvs, scFv4-2 and scFv22-1, exhibited moderate to higher binding with sub-micromolar $EC_{50}$s to five ebolavirus glycoproteins and a marburgvirus glycoproteins (FIG. 4A, 4B). scFv4-2 antibody showed an approximate two-fold greater affinity to all glycoproteins compared to the scFv22-1 antibody (FIG. 7, Table 2).

Western blot analysis suggests that the conformational epitopes recognized by scFv4-2 and scFv22-1 are completely destroyed when glycoproteins are denatured (FIG. 5). scFv4-2 and scFv 22-1 recognized MARV glycoprotein, suggesting that these scFvs bind to a different epitope than the epitope in glycoproteins of EBOV, SUDV, BDBV, and RESTV. These scFvs bound to all six native glycoproteins in an ELISA, but not a Western Blot, suggesting these scFvs can recognize glycoproteins in its natural conformation and binds to conformational epitopes.

Immunoprecipitation analysis using lysates of filovirus glycoproteins produced in 293T cells (FIG. 6) produced cross-reactivity profiles and virus specificities that were similar to those obtained by ELISA. cFv4-2 and scFv22-1 cross react to marburgvirus and all known ebolaviruses.

Although a previous study demonstrated in vivo efficacy of anti-marburgvirus glycoprotein scFvs (Froude et al., 2017, *MAbs* 9(4):696-703), this disclosure reports scFvs, scFv4-2 and scFv22-1, that exhibit broad cross-reactive activity against filovirus glycoprotein. These scFvs also have the potential for identifying as yet unknown Ebolavirus species. The scFvs generated in this study may therefore offer some advantage in generating a highly sensitive assay for diagnostic use.

In summary, a panel of scFvs that specifically bind to filovirus glycoproteins were generated by ribosome display and cross-reactivity profiles of the scFvs across all known human pathogenic filoviruses was established. The ribosome display method described herein is inexpensive, rapid, and can be used to quickly develop repertoires of high-affinity antibodies. The scFvs described herein can detect all known ebolaviruses and marburgviruses. Thus, the broadly cross-reactive scFvs produced in this study have great diagnostic and/or therapeutic potential.

Thus, in one aspect, this disclosure describes antibodies that specifically bind to filovirus glycoproteins—e.g., ebolavirus glycoproteins and marburgvirus glycoproteins. While described herein in the context of an scFv antibody fragment, the antibodies and methods described herein can involve any suitable antibody or antibody fragment. Thus, the term "antibody" refers to a molecule that contains at least one antigen binding site that immunospecifically binds to a particular antigen target of interest. The term "antibody" thus includes, but is not limited to, a full length antibody and/or its variants, a fragment thereof, peptibodies and variants thereof, monoclonal antibodies (including full-length monoclonal antibodies), multispecific antibodies (e.g., bispecific antibodies, trispecific antibodies, etc.), human antibodies, humanized antibodies, and antibody mimetics that mimic the structure and/or function of an antibody or a specified fragment or portion thereof, including single chain antibodies and fragments thereof. Thus, as used herein, the term "antibody" encompasses antibody fragments capable of binding to a biological molecule (such as an antigen or receptor) or a portion thereof, including but not limited to Fab, Fab' and F(ab')$_2$, pFc', Fd, a single domain antibody (sdAb), a variable fragment (Fv), a single-chain variable fragment (scFv) or a disulfide-linked Fv (sdFv); a diabody or a bivalent diabody; a linear antibody; a single-chain antibody molecule; and a multispecific antibody formed from antibody fragments. The antibody can be of any type (e.g., IgG, IgE, IgM, IgD, IgA and IgY), class (e.g., IgG1, IgG2, IgG3, IgG4, IgA1 and IgA2), or subclass.

In some embodiments, the antibody can include the amino acid sequence of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, or SEQ ID NO:36. In some embodiments, the antibody can include a fragment of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or a combination of two or more such fragments. In certain embodiments, a fragment of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, or SEQ ID NO:36 can include the CDR1 $V_H$, CDR2 $V_H$, CDR3 $V_H$, CDR1 $V_L$, CDR2 $V_L$, or CDR3 $V_L$ of the identified SEQ ID NO, as shown in FIG. 9.

In another aspect, this disclosure describes methods of detecting a filovirus in a biological sample obtained from a subject. Generally, the method includes obtaining the biological sample from the subject, contacting a filovirus antibody as described herein with the biological sample under conditions effective to allow the antibody to bind to filovirus in the sample, thereby forming an antibody:target complex, and detecting the antibody:target complex.

In some embodiments, the filovirus can be an ebolavirus. In other embodiments, the filovirus can be a marburgvirus.

The antibody:target complex can be detected using any suitable method. Suitable methods include, but are not limited to, performing an enzyme-linked immunoassay (ELISA), performing Western blot analysis, or performing an immunofluorescence assay. An ELISA or immunofluorescence assay may be performed using a secondary antibody that includes a fluorescent tag. Alternatively, an ELISA or immunoassay may be performed by designing the filovirus antibody to include as fluorescent tag such those described in U.S. Pat. No. 8,877,898.

In yet another aspect, this disclosure describes methods of treating a subject having, or at risk of having, a filovirus infection. As used herein, the term "treat" or variations thereof refer to reducing, limiting progression, ameliorating, or resolving, to any extent, the symptoms or signs related to a condition. A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject.

Also as used herein, the term "at risk" refers to a subject that may or may not actually possess the described risk. Thus, for example, a subject "at risk" of infection by a filovirus is a subject present in an area where individuals have been identified as infected by a filovirus and/or where an individual is likely to be exposed to the filovirus even if the subject has not yet manifested any detectable indication of infection by a filovirus and regardless of whether the subject may harbor a subclinical amount of a filovirus.

An anti-filovirus-glycoprotein antibody as described herein may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with the antibody without causing any undesirable biological effects or interacting in a deleterious manner with any of the other components of the pharmaceutical composition in which it is contained.

An anti-filovirus-glycoprotein antibody as described herein may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, an anti-filovirus-glycoprotein antibody as described herein may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the anti-filovirus-glycoprotein antibody into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of antibody administered can vary depending on various factors including, but not limited to, the specific anti-filovirus-glycoprotein antibody being administered, the weight, physical condition, and/or age of the subject, and/or the route of administration. Thus, the absolute weight of antibody included in a given unit dosage form can vary widely, and depends upon factors such as the species, age, weight and physical condition of the subject, and/or the method of administration. Accordingly, it is not practical to set forth generally the amount that constitutes an amount of antibody effective for all possible applications. Those of ordinary skill in the art, however, can readily determine the appropriate amount with due consideration of such factors.

In some embodiments, the method can include administering sufficient anti-filovirus-glycoprotein antibody to provide a dose of, for example, from about 100 ng/kg to about 50 mg/kg to the subject, although in some embodiments the methods may be performed by administering antibody in a dose outside this range. In some of these embodiments, the method includes administering sufficient antibody to provide a dose of from about 10 µg/kg to about 5 mg/kg to the subject, for example, a dose of from about 100µm/kg to about 1 mg/kg.

Alternatively, the dose may be calculated using actual body weight obtained just prior to the beginning of a treatment course. For the dosages calculated in this way, body surface area (m$^2$) is calculated prior to the beginning of the treatment course using the Dubois method: $m^2$=(wt $kg^{0.425}$×height $cm^{0.725}$)×0.007184.

In some embodiments, the method can include administering sufficient anti-filovirus-glycoprotein antibody to provide a dose of, for example, from about 0.01 mg/m$^2$ to about 10 mg/m$^2$.

In some embodiments, the antibody may be administered, for example, from a single dose to multiple doses per week, although in some embodiments the method can be performed by administering the antibody at a frequency outside this range. When multiple doses are used within a certain period, the amount of each dose may be the same or different. For example, a dose of 1 mg per day may be administered as a single dose of 1 mg, two 0.5 mg doses, or as a first dose of 0.75 mg followed by a second dose of 0.25 mg. Also, when multiple doses are used within a certain period, the interval between doses may be the same or be different.

In certain embodiments, the antibody may be administered from a single, one-off administration to multiple times per week. For prophylactic treatments, an initial dose may be followed by a booster dose. Boosting doses, when administered, are adequately spaced (e.g., yearly) to boost the level of circulating antibody that has fallen below a desired level. Boosting doses may include an anti-filovirus-glycoprotein antibody either with or in the absence of an adjuvant.

In some cases, the method can further include administering to the subject an additional therapeutic agent effective for treating infection by a filovirus.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Plasmids, Strains and Reagents

All reagents used in the study were commercially available and were of reagent grade or better. All restriction enzymes and DNA modification enzymes were of molecular biology grade. All primers were purchased from Invitrogen (Carlsbad, CA). pGEM-T easy cloning vector (Cat. #A1360) and TNT T7 Quick for PCR DNA kit (rabbit reticulocyte cell free extract, Cat. #L5540) were purchased from Promega Corp. (Madison, WI). Plasmid pBAK1 was constructed as previously described (Markiv et al., 2011, J Immunol Methods 364(1-2):40-49). Rabbit anti-Strep tag II polyclonal antibody affinity purified HRP conjugated (Cat. #A01742-100, GenScript Piscataway, NJ), mouse anti-his antibody (Cat. #A00186-100, Invitrogen, Carlsbad, CA) and rabbit anti-mouse AP antibody (Cat. #SAB3701085, Sigma-Aldrich, St. Louis, MO) were commercially available. AP detection reagent kit (Cat. #69264-3) was purchased from MilliporeSigma, (Burlington, MA).

Cell Lines and Plasmids

HEK293T cells (American Type Culture Collection, Manassas, Va.) were maintained in Dulbecco's Modified Eagle Medium (DMEM; Gibco)+10% fetal bovine serum (FBS)+1% penicillin/streptomycin. Filovirus glycoproteins were encoded in pcDNA3.1 plasmids. Ebola VLPs. eVLPs were prepared essentially as previously described, with minor modifications (Ayithan et al., 2014, *J Interferon Cytokine Res* 34(2):79-89; Ayithan et al., 2015, *PLoS One* 10(2):e0118345). Plasmids expressing EBOV-Yambuku GP1,2 and VP40 were transfected into 293T cells using JETPRIME (Polyplus Transfection, New York, NY), according to the manufacturer's protocol. Three days after transfection, supernatants were harvested and centrifuged at 9,000×g for two hours. VLP pellets were resuspended in PBS and layered for a discontinuous 60/30/10 gradient, and ultracentrifuged for 18 hours at 150,000×g. Lower bands were collected, diluted in PBS, and centrifuged for two hours at 100,000×g. Pellets were resuspended in PBS, and quantitated.

Immunization of Mice

C57BL/6 mice were obtained from The Jackson Laboratory (Bar Harbor, ME). Mice were vaccinated intraperitoneally with 10 µg of EBOV virus-like particles (VLPs) mixed with alum twice at three-week intervals. Splenocytes of individual mice were placed in 10 mL of TRIzol for use in RNA isolation approximately six weeks after the last vaccination.

Antibody Library Construction

Total spleen RNA was prepared previously described (Andris-Widhopf et al., 2001, *Phage Display: A Laboratory Manual*. Barbas III C F, Burton D R, Scott J K and Silverman G J (eds). Cold Spring Harbor Laboratory Press: Plainview, NY, pp. 9.1-9.113). Mouse spleens were minced and homogenized in 10 mL TRIzol (Invitrogen, Carlsbad, CA). The total RNA pellet was air-dried and resuspended in 500 µL of nuclease-free water (stored at −80° C.). Complementary DNA (cDNA) was synthesized from approximately 25 μg of total RNA using a SUPERSCRIPT II RT (Invitrogen, Carlsbad, CA) following the manufacturer's instructions.

For antibody library construction, the PCR primers were based on published sequences with minor modifications (Table 1). The primers were designed to introduce in-frame NcoI and NotI restriction sites to the 5' end of the $V_H$ sequence and to the 3' end of the VL sequence, respectively. The VH_F/VH_R and VL_F/VL_R sets of primers (Table 1) were used for PCR amplification of VH and VL gene segments using the cDNA template. The VH_R and VL_F set of primers (Table 1) were used to introduce overlapping sequences which enabled the scFv gene fragments to be assembled by overlap extension PCR and these primers encode a 20 amino acid linker sequence $(G_4S)_4$. The amplified heavy and light-chain products were purified and pooled, and an aliquot of light and heavy-chain templates was subjected to overlap extension PCR amplification using Link to introduce Strep II tag and Kozak sequence on the 5' end and an overlap extension on the 3' end to facilitate joining to the variable heavy-chain libraries using MKR and KzSTREPII. Finally, the PCR product encoding all the variable heavy-chain and light-chain combinations was amplified with primers RDT7 and MKR to introduce T7 site into Strep tag II-conjugated VH-VL library and to produce the DNA encoding the anti-Ebola immunoglobulin scFv libraries. The initial PCR amplification reactions were performed at a 52° C. annealing temperature with 30 cycles, and the subsequent library assembly step used 16 cycles with GoTaq DNA polymerase and 20 pmoL of each primer pair per reaction. DNA fragments were resolved by gel electrophoresis on 1% (wt/vol) agarose gels. DNA isolation from agarose gels was carried out following QIAquick DNA gel purification kit instructions. The final purified PCR product ~0.9 kb is a template for Ribosome Display.

TABLE 1

Nucleotide sequence of primers

| Primer name | Primer sequence (5'-3') | SEQ ID NO: |
|---|---|---|
| | VH primers | |
| MVH_F1 | CGAGAAGACCGGCAGCGGTGGGGCAGAGCTTGTGAAGCCA | 1 |
| MVH_F2 | CGAGAAGACCGGCAGCGGTGGAGGAGGCTTGATGCAACCT | 2 |
| MVH_F3 | CGAGAAGACCGGCAGCGGTGGACCTGAGCTGGAGATGCCT | 3 |
| MVH_F4 | CGAGAAGACCGGCAGCGGTGGACCTGGCCTGGTGAGACCT | 4 |
| MVH_F5 | CGAGAAGACCGGCAGCGGTGGGGGAGGCTTAGTGAAGCCT | 5 |
| MVH_F6 | CGAGAAGACCGGCAGCGGTGGGGCAGAGCTTGTGAAGCCA | 6 |
| MVH_F7 | CGAGAAGACCGGCAGCGGTGGAGGGGGCTTGGTACAGCCT | 7 |
| MVH_F8 | CGAGAAGACCGGCAGCGGTGGGGCAGAGCTTGTGAGGTCA | 8 |
| MVH_R1 | GGAGCCGCCGCCGCCGCCAGAACCACCACCACC***GGATCC*** ACCACCACCCGAGGA AACGGTGACCGTGGT | 9 |
| MVH_R2 | GGAGCCGCCGCCGCCGCCAGAACCACCACCACC***GGATCC*** ACCACCACCCGAGGA GACTGTGAGAGTGGT | 10 |
| MVH_R3 | GGAGCCGCCGCCGCCGCCAGAACCACCACCACC***GGATCC*** ACCACCACCCGCAGA GACAGTGACCAGAGT | 11 |
| MVH_R4 | GGAGCCGCCGCCGCCGCCAGAACCACCACCACC***GGATCC*** ACCACCACCCGAGGA GACGGTGACTGAGGT | 12 |
| | VL primers | |
| MVL_F1 | GGCGGCGGCGGCTCCGGTGGTGGT***GGATCC*** GCAATCATGTCTGCATCTCC | 13 |
| MVL_F2 | GGCGGCGGCGGCTCCGGTGGTGGT***GGATCC*** GCCTCCCTATCTGTATCTGTG | 14 |
| MVL_F3 | GGCGGCGGCGGCTCCGGTGGTGGT***GGATCC*** GCCTCCCTATCTGCATCTGTG | 15 |
| MVL_F4 | GGCGGCGGCGGCTCCGGTGGTGGT***GGATCC*** CTCACTTTGTCGGTTACCATT | 16 |
| MVL_F5 | GGCGGCGGCGGCTCCGGTGGTGGT***GGATCC*** TCAGCCTCTTTCTCCCTGGGA | 17 |
| MVL_F6 | GGCGGCGGCGGCTCCGGTGGTGGT***GGATCC*** TCCTCCCTGAGTGTGTCAGCA | 18 |
| MVL_F7 | GGCGGCGGCGGCTCCGGTGGTGGT***GGATCC*** CTCTCCCTGCCTGTCAGTCTT | 19 |
| MVL_F8 | GGCGGCGGCGGCTCCGGTGGTGGT***GGATCC*** CTCTCCCTGCCTGTCAGTCTT | 20 |

TABLE 1-continued Nucleotide sequence of primers

| Primer name | Primer sequence (5'-3') | SEQ ID NO: |
|---|---|---|
| MKR | AGAACACTCATTCCTGTTGAAGCTCTTGACAATGGGTGAAGTTG | 21 |
| MKR_NotI | AGTGCGGCCGCAGAACACTCATCCTGTTGAAGCTCTTGACAATGGGTGAAGTTG | 22 |
| | Strep Tag II | |
| KzSTREPII | CGAATTCCACCATGGCC TGG AGC CAT CCG CAG TTC GAG AAG ACC GGC AGC GG | 23 |
| | T7 promoter | |
| RDT7 | CTATAGAAGG GTAATACGACTCACTATAGGGCGAATTCCACCATGGCC | 24 |

Cell-Free Ribosome Display Technology

To select specific antibody fragments, a modified eukaryotic ribosome display with slight modifications was used (He et al., 2007, *Nature Methods* 4(3):281-288). In vitro transcription and translation reaction was based on a coupled rabbit reticulocyte lysate system (TNT quick-coupled transcription-translation system, Promega Corp., Madison, WI) and performed according to the supplier's protocol. The PCR-generated DNA library of antibody-coding genes derived from mouse 1 were expressed in this lysate system. Briefly, 50 µL of transcription/translation mixture containing 40 µL of TNT T7 Quick Master Mix, 2 µL of DNA library (0.1 µg to 1.0 µg), 1 µL (1 mM) of methionine, 1 µL of DNA enhancer, and 6 µL of water were added, and the reaction mixture was incubated at 30° C. for 90 minutes. Then, 5 µL of RNase-free DNase I (Roche, Basel, Switzerland) (2,000 U/ml) was added, and the mixture was incubated for 20 minutes at 30° C. (in order to remove the DNA template so that subsequent PCR only picks up pulled down RNA sequences).

To select specific antibody fragments, the 0.5 mL PCR tubes were coated with 1 µg/mL of the recombinant Zaire Ebov glycoprotein in 100 µL PBS at 4° C. overnight. Protein-coated tubes were washed with PBS and blocked with 100 µL of molecular biology grade bovine serum albumin (BSA) in PBS (10 mg/mL) (New England Biolabs, Inc., Ipswich, MA) for one hour at room temperature. The translation/transcription mixture (containing the protein-ribosome-mRNA (PRM) complexes) was added to the washed and blocked protein-coated tubes and incubated on ice for one hour. The PCR tubes were washed three times with ribosome display washing buffer (PBS containing 0.01% Tween 20, 5 mM magnesium acetate and 0.1% BSA, pH 7.4) and two times quick wash with ice-cold RNase-free water, and the retained RNA (antibody sequences) subjected to the following recovery process; in situ Single-Primer RT-PCR Recovery was performed in the PCR tubes carrying selected ARM complexes using a SuperScript II reverse transcriptase (Invitrogen, Carlsbad, CA). The obtained cDNA was amplified in a 25 µL PCR mixture for 35 cycles of 30 seconds at 94° C., 30 seconds at 52° C., and one minute at 72° C., and 10 minutes at 72° C. with MKR and KzStrep II using GoTaq DNA polymerase (Promega Corp., Madison, WI). The RT-PCR product from a single round of ribosome display was purified by agarose gel electrophoresis.

Cloning, Expression and Purification of an Anti-Ebov Glycoprotein scFvs

The RT-PCR product from a third round of ribosome display was cloned into the pGEM-T Easy vector (T-CLONING kit, Promega Corp., Madison, Wis.) according to the manufacturer's instructions. The ligation products were transformed in pGEM-T Easy vector *E. coli* cells and positive colonies were chosen by blue-white selection and confirmed by DNA sequencing using T7 and SP6 standard primers (Table 1). Based on the sequencing results, the clones in right reading frame without stop codon were chosen for prokaryotic expression. EbovGP-scFv is expressed in the form of C-terminal 6×His fusion from the prokaryotic expression vector pBAK1 (Markiv et al., 2011, *J Immunol Methods* 364(1-2):40-49). This vector has a strong T7 promoter, and is designed to work with Rosetta-gami (DE3) strains of *E. coli*. The protein is induced and expressed at room temperature (25° C.), to increase the portion of the correctly folded, soluble EbovGP-scFv.

For the construct of scFvs, DNA was amplified with the forward primer, KzStrepII 5'CGAATTCCAC-CATGGCCTGGAGCCATCCGCAGTTCGAGAA-GACCGGCAGCGG3' (SEQ ID NO:25; with an NcoI restriction sequence underlined) and the reverse primer, MKR NotI 5'AGTGCGGCCGCAGAACACT-CATCCTGTTGAAGCTCTTGACAATGGGT-GAAGTTG3' (SEQ ID NO:26; with an NotI restriction sequence underlined). Both set of primers allow these two amplicons (FIG. 8) to be subcloned into a pBAK1-His vector (Markiv et al., 2011, *J Immunol Methods* 364(1-2): 40-49) and were transformed into Rosetta gami B(DE3) *E. coli* strain and plated onto LB agar plate with 100 µg/mL of carbenicillin, and grown at 37° C. for 16 hours.

The molecular weight and isoelectric points was predicted using ExPASy bioinformatics resource portal (Gasteiger et al., 2003, *Nucleic Acids Res* 31(13):3784-3788). Next day, five colonies were inoculated in 3 mL of LB media with the same antibiotics and grown at 37° C. with 225 rpm shaking for 16-18 hours. and the positive clones were selected by restriction analysis with NcoI and NotI and confirmed by DNA sequencing. The 3 mL overnight culture was used to prepare a glycerol bacterial stock and inoculated into 200 mL of LB medium containing the same antibiotics and grown at 37° C. with shaking at 225 rpm until $OD_{600}$ reached between 0.4-0.6. The culture was briefly chilled on ice to 25° C. and the cells were induced by the addition of IPTG (final concentration 1 mM) and were incubated for 12 hours at 25° C. with shaking. Cells were harvested in 4×50 mL tubes by centrifugation at 4000×g at 4° C. for 20 minutes. Cell pellets were frozen and stored at −80° C. before undergoing further processing.

The 50 mL cell pellet from 200 mL culture was re-suspended in 3 mL of lysis buffer (20 mM Tris-HCl, 500 mM NaCl, 20 mM imidazole, 0.1% Triton X-100 pH 8.0). Cells were lysed by sonication on ice (6×30 seconds), and were centrifuged at 14,000×g for 15 minutes to remove cellular debris. The soluble fraction was filtered through 0.2 µm filters and applied to HisTrap excel 1 mL column (GE Life Sciences, Marlborough, MA.). The column was equilibrated and washed with 20 mM Tris-HCl, 500 mM NaCl, 20 mM imidazole pH 8.0 and the sample was eluted 20 mM Tris-HCl, 500 mM NaCl, 500 mM imidazole, pH 8.0 in one elution step. The purification was carried out at a constant flow of 1 mL/minute. Fractions of 1 mL were collected through the elution step. The purified protein fractions were kept at 4° C.

Western Blot of scFv Fragments

The proteins were separated by SDS-PAGE and were blotted onto polyvinylidene difluoride (PVDF) membrane using a iBlot2 Gel TransferDevice (Life Technologies, Carlsbad, CA) for seven minutes. The membranes were blocked in 5% w/v skimmed milk powder/TBS buffer at room temperature for one hour, then incubated with mouse anti-His antibody (GenScript, Piscataway, NJ) at a dilution of 1:5000 for one hour. After three washes with Tris-buffered saline/polysorbate 20 (TBST) buffer, the membranes were incubated with horseradish-peroxidase (HRP)-conjugated rabbit anti-strep tag II antibody (diluted 3/10,000 in TBST) (GenScript, Piscataway, NJ) at room temperature for one hour, followed by washing with TBST buffer three times for 10 minutes each. The protein was detected and visualized with ECL detection reagent (Amersham, GE Healthcare, Chicago, IL) following the manufacturer's recommendation.

Transfections

All transfections were performed in HEK293T cells seeded in a 6-well plate (PMID 29118454 Cells were transfected with filovirusGPs (sequences listed in PMID 29118454) using JETPRIME (Polyplus Transfection, New York, NY) according to the manufacturer's recommendations. Cells were stained with antibodies 48 hours after transfection. Specificity, cross-reactivity and affinity of glycoprotein-specific scFvs To determine binding and cross-reactivity and half maximal effective concentrations, or $EC_{50}$s, scFvs were tested for binding to the glycoprotein antigens (1 µg/ml) of EBOV, SUDV, BDBV, and RESTV, as well as to MARV Ravn glycoprotein at a concentration range of 30 µg/ml to 0.1 µg/ml. ELISAs were performed as follows: Nunc Polysorp ELISA plates were coated overnight at 4° C. either with target filovirus glycoprotein antigens, blocked with 2% BSA at 37° C. for one hour and incubated with anti-EBOV scFvs in 1% BSA. Commercial monoclonal (Mouse anti-EBOV antibody 6D8, and Mouse anti-SUDV ebola virus antibody) and polyclonal (Rabbit anti-RESTV GP, Rabbit anti-BDBV GP, Rabbit anti-MARV GP, and Rabbit anti-TAFV GP) antibodies were served as positive controls, whereas Mouse anti-PilB scFv21 antibody (unpublished data) as negative control. After a one-hour incubation at 37° C., plates were washed as described above and scFv was detected with HRP-conjugated Rabbit anti-strep tag II polyclonal antibody in PBS containing 1% BSA and incubated at 37° C. for one hour. After washing and tap drying, 100 µL of TMB substrate was added to each well and the plate was allowed to incubate for 15-30 minutes at 25° C. The reaction was stopped with 0.18 M $H_2SO_4$, and absorbance reading was measured at 450 nm and these values were transformed using Softmax Pro (7.1) 4 parameter curve-fit (Molecular Devices, LLC, San Jose, CA).

Western Blot Analysis

Different purified pan-ebola and pan-filovirus antigens [Lloviu virus (LLOV), ZEBOV, SUDV, RESV, BDBV, MARV, and TAFV glycoproteins] of 1 µg/mL were separated on 4-12% SDSPAGE and transferred onto PVDF transfer membrane using a iBlot2 Gel TransferDevice (Life Technologies, Carlsbad, CA) for seven minutes. The membranes were blocked with 5% skim milk in TBS, 0.1% Tween-20 (TBST) for two hours followed by incubation with the scFv 4-2 or scFv 22-1 (1 µg/ml concentration) diluted in Tris-buffered saline/polysorbate 20 (TBST) for one hour. After three washes with TBST, the membranes were incubated with HRP-conjugated rabbit anti-strep tag II antibody (diluted 3:10,000 in 5% Milk/TBS) (GenScript, Piscataway, NJ) at room temperature for one hour, followed by washing with TBS-T buffer three times for 10 minutes each. The protein was detected and visualized with ECL detection reagent as described above.

Immunoprecipitation Assay (IP)

EBOVHEK293, SUDVHEK293, RESVHEK293, BDBVHEK293, MARVHEK293, LLOVHEK293 and HEK293 cell lysates (containing 10 mg protein) were obtained by lysis with NP40 buffer, protease inhibitor cocktail, and PMSF and incubated with 25 µg Strep tag-fusion proteins (scFvs 4-2 and 22-1) and left rotating overnight at 4° C. overnight. Following overnight rotation, 40 µl of Strep 2 Mag beads (IBA) were added to the cell lysates and rotated at 4° C. for one hour. The samples were then centrifuged at 3,000 rpm for one minute at 4° C. and supernatant discarded. Samples were then washed four times in 1 mL of Buffer W buffer by centrifuging at 3,000 rpm at 4° C. for one minute and discarding the supernatant each time. 50 µL of Laemmli sample buffer was added to the samples, heated to 85° C. for two minutes, centrifuged at 13,000 rpm for 10 minutes and resolved by SDS-PAGE and immunoblot as described above. The membranes were blocked with 5% non-fat dry milk. Membranes (immunoprecipitated complexes) were probed with the mouse (anti-Zaire ebola antibody 6D8, anti-Sudan ebola virus antibody, and anti-His antibody) and rabbit (anti-Reston GP polyclonal antibody, anti-Bundibugyo GP polyclonal antibody, anti-MARV GP polyclonal antibody, and anti-Tai Forest virus GP IgG) as primary antibodies at a dilution of 1:5000 and the HRP-conjugated donkey anti-mouse and goat anti-rabbit as secondary antibodies at a dilution of 1:3000 diluted in TBST was added for a one-hour incubation.

Immunofluorscence Assay (IFA)

The EBOV, SUDV, BDBV, RESTV, and TAFV viruses were inoculated into 293T cells seeded in eight wells chamber slides (BD Biosciences, San Jose, Calif.). Forty-eight hours post inoculation infected cells were fixed with 4% paraformaldehyde solution for 10 minutes at room temperature. After fixation slides were washed three times with PBS, three minutes per wash, and blocked with PBS-0.1% BSA. Then cells were washed and incubated for one hour at room temperature with a 1:100 dilution of the ZEBOVGP scFvs 4-2 and 22-1 (500 µg/mL). After incubation, cells were washed three times with PBS, three minutes per wash. Cells were incubated at room temperature with a 1:200 dilution of goat anti-Mouse IgG Secondary Antibody, Alexa Fluor 488 (Thermo Fisher Scientific Inc., Waltham, Mass.) diluted in blocking buffer (PBS with 0.1% of BSA) for one hour at room temperature. Cells were washed three times as described above, air dried, and covered with DABCO polyvinyl alcohol mounting medium (Sigma-Aldrich, St. Louis, MO), followed by fluorescent microscope examination.

Binding Constant (KD) Determinations

The values for apparent affinity ($K_d$,app) and maximal binding ($B_{max}$, shown as relative absorbance units) were derived from the ELISAs with $GP_{ZEBOV}$, $GP_{SUDV}$, $GP_{RESTV}$, $GP_{BDBV}$, $GP_{TAFV}$ and $GP_{MARV}$. Values are averages (and ranges) of three experiments.

TABLE 2

Apparent affinity and maximal binding of EBOVGP scFvs to $GP_{ZEBOV}$, $GP_{SUDV}$, $GP_{RESTV}$, $GP_{BDBV}$, $GP_{TAFV}$ and $GP_{MARV}$.

| | scFv4-2 | | scFv22-1 | |
|---|---|---|---|---|
| GP | $K_d$, app (μg) | $B_{max}$ signal ($10^5$) | $K_d$, app (μg) | $B_{max}$ signal ($10^5$) |
| ZEBOV | 4.8 ± 1.5 | 3.5 ± 0.3 | 9.3 ± 1.2 | 3.7 ± 0.2 |
| SUDV | 6.6 ± 0.9 | 2.8 ± 0.1 | 10.8 ± 1.6 | 2.8 ± 0.2 |
| RESTV | 12.2 ± 3.4 | 2.1 ± 0.2 | 17.4 ± 4.2 | 3.2 ± 0.4 |
| BDBV | 15.1 ± 4.8 | 2.2 ± 0.3 | 38 ± 23 | 4.6 ± 1.8 |
| TAFV | 8.2 ± 0.8 | 2.8 ± 0.1 | 19.3 ± 4.3 | 2.7 ± 0.3 |
| MARV | 5.9 ± 1.8 | 3.8 ± 0.3 | 10.8 ± 3.8 | 2.5 ± 0.3 |

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. An antibody comprising:
    Complementarity Determining Region (CDR) 1 variable heavy chain ($V_H$) of EbovGPscFv4-2 (SEQ ID NO:30);
    CDR2 $V_H$ of EbovGPscFv4-2 (SEQ ID NO:30);
    CDR3 $V_H$ of EbovGPscFv4-2 (SEQ ID NO:30);
    CDR1 variable light chain ($V_L$) of EbovGPscFv4-2 (SEQ ID NO:30);
    CDR2 $V_L$ of EbovGPscFv4-2 (SEQ ID NO:30); or
    CDR3 $V_L$ of EbovGPscFv4-2 (SEQ ID NO:30).

2. The antibody of claim 1, wherein the antibody is an antibody fragment.

3. The antibody of claim 1, wherein the antibody binds to a filovirus.

4. The antibody of claim 3, wherein the antibody binds to at least one of: Ebola virus (EBOV) glycoprotein, Sudan ebolavirus (SUDV) glycoprotein, Reston ebolavirus (RESTV) glycoprotein, Bundibugyo ebolavirus (BDBV) glycoprotein, Marburg ebolavirus (MARV) glycoprotein, or Tai Forest ebolavirus (TAFV) glycoprotein.

5. The antibody of claim 3, wherein the antibody binds to EBOV glycoprotein, SUDV glycoprotein, RESTV glycoprotein, BDBV glycoprotein, MARV glycoprotein, and TAFV glycoprotein.

6. A method of detecting a filovirus in a biological sample obtained from a subject, the method comprising:
    obtaining the biological sample from the subject;
    contacting the antibody of claim 1 with the biological sample under conditions effective to allow the antibody to bind to filovirus in the sample, thereby forming an antibody: target complex; and
    detecting the antibody: target complex.

7. The method of claim 6, wherein the filovirus is an ebolavirus.

8. The method of claim 6, wherein the filovirus is a marburgvirus.

9. The method of claim 6, wherein detecting the antibody: target complex comprises performing an enzyme-linked immunosorbent assay (ELISA).

10. The method of claim 6, wherein detecting the antibody: target complex comprises performing Western blot analysis.

11. The method of claim 6, wherein detecting the antibody: target complex comprises performing an immunofluorescence assay.

12. A method of treating a subject having, or at risk of having, a filovirus infection, the method comprising:
    administering to the subject an effective amount of a pharmaceutical composition comprising the antibody of claim 1.

13. The method of claim 12, wherein the pharmaceutical composition is administered before the subject exhibits a symptom or clinical sign of having a filovirus infection.

14. The method of claim 12, wherein the pharmaceutical composition is administered after the subject exhibits a symptom or clinical sign of having a filovirus infection.

15. The method of claim 12, wherein the filovirus is an ebolavirus.

16. The method of claim 12, wherein the filovirus is a marburgvirus.

* * * * *

SEQUENCE LISTING

```
<160> NUMBER OF SEQ ID NOS: 36

<210> SEQ ID NO 1
<211> LENGTH: 40
<212> TYPE: DNA
<213> ORGANISM: artificial
<220> FEATURE:
<223> OTHER INFORMATION: Primer

<400> SEQUENCE: 1
cgagaagacc ggcagcggtg gggcagagct tgtgaagcca                          40

<210> SEQ ID NO 2
<211> LENGTH: 40
<212> TYPE: DNA
<213> ORGANISM: artificial
<220> FEATURE:
<223> OTHER INFORMATION: Primer

<400> SEQUENCE: 2
cgagaagacc ggcagcggtg gaggaggctt gatgcaacct                          40

<210> SEQ ID NO 3
<211> LENGTH: 40
<212> TYPE: DNA
<213> ORGANISM: artificial
<220> FEATURE:
<223> OTHER INFORMATION: Primer

<400> SEQUENCE: 3
cgagaagacc ggcagcggtg gacctgagct ggagatgcct                          40
```

-continued

```
<210> SEQ ID NO 4
<211> LENGTH: 40
<212> TYPE: DNA
<213> ORGANISM: artificial
<220> FEATURE:
<223> OTHER INFORMATION: Primer

<400> SEQUENCE: 4
cgagaagacc ggcagcggtg gacctggcct ggtgagacct                             40

<210> SEQ ID NO 5
<211> LENGTH: 40
<212> TYPE: DNA
<213> ORGANISM: artificial
<220> FEATURE:
<223> OTHER INFORMATION: Primer

<400> SEQUENCE: 5
cgagaagacc ggcagcggtg ggggaggctt agtgaagcct                             40

<210> SEQ ID NO 6
<211> LENGTH: 40
<212> TYPE: DNA
<213> ORGANISM: artificial
<220> FEATURE:
<223> OTHER INFORMATION: Primer

<400> SEQUENCE: 6
cgagaagacc ggcagcggtg gggcagagct tgtgaagcca                             40

<210> SEQ ID NO 7
<211> LENGTH: 40
<212> TYPE: DNA
<213> ORGANISM: artificial
<220> FEATURE:
<223> OTHER INFORMATION: Primer

<400> SEQUENCE: 7
cgagaagacc ggcagcggtg gaggggggctt ggtacagcct                            40

<210> SEQ ID NO 8
<211> LENGTH: 40
<212> TYPE: DNA
<213> ORGANISM: artificial
<220> FEATURE:
<223> OTHER INFORMATION: Primer

<400> SEQUENCE: 8
cgagaagacc ggcagcggtg gggcagagct tgtgaggtca                             40

<210> SEQ ID NO 9
<211> LENGTH: 69
<212> TYPE: DNA
<213> ORGANISM: artificial
<220> FEATURE:
<223> OTHER INFORMATION: Primer

<400> SEQUENCE: 9
ggagccgccg ccgccgccag aaccaccacc accggatcca ccaccacccg aggaaacggt       60
gaccgtggt                                                              69

<210> SEQ ID NO 10
<211> LENGTH: 69
<212> TYPE: DNA
<213> ORGANISM: artificial
<220> FEATURE:
```

```
<223> OTHER INFORMATION: Primer

<400> SEQUENCE: 10
ggagccgccg ccgccgccag aaccaccacc accggatcca ccaccacccg aggagactgt    60
gagagtggt                                                           69

<210> SEQ ID NO 11
<211> LENGTH: 69
<212> TYPE: DNA
<213> ORGANISM: artificial
<220> FEATURE:
<223> OTHER INFORMATION: Primer

<400> SEQUENCE: 11
ggagccgccg ccgccgccag aaccaccacc accggatcca ccaccacccg cagagacagt    60
gaccagagt                                                           69

<210> SEQ ID NO 12
<211> LENGTH: 69
<212> TYPE: DNA
<213> ORGANISM: artificial
<220> FEATURE:
<223> OTHER INFORMATION: Primer

<400> SEQUENCE: 12
ggagccgccg ccgccgccag aaccaccacc accggatcca ccaccacccg aggagacggt    60
gactgaggt                                                           69

<210> SEQ ID NO 13
<211> LENGTH: 50
<212> TYPE: DNA
<213> ORGANISM: artificial
<220> FEATURE:
<223> OTHER INFORMATION: Primer

<400> SEQUENCE: 13
ggcggcggcg gctccggtgg tggtggatcc gcaatcatgt ctgcatctcc              50

<210> SEQ ID NO 14
<211> LENGTH: 51
<212> TYPE: DNA
<213> ORGANISM: artificial
<220> FEATURE:
<223> OTHER INFORMATION: Primer

<400> SEQUENCE: 14
ggcggcggcg gctccggtgg tggtggatcc gcctccctat ctgtatctgt g            51

<210> SEQ ID NO 15
<211> LENGTH: 51
<212> TYPE: DNA
<213> ORGANISM: artificial
<220> FEATURE:
<223> OTHER INFORMATION: Primer

<400> SEQUENCE: 15
ggcggcggcg gctccggtgg tggtggatcc gcctccctat ctgcatctgt g            51

<210> SEQ ID NO 16
<211> LENGTH: 51
<212> TYPE: DNA
<213> ORGANISM: artificial
<220> FEATURE:
<223> OTHER INFORMATION: Primer
```

<400> SEQUENCE: 16
ggcggcggcg gctccggtgg tggtggatcc ctcactttgt cggttaccat t    51

<210> SEQ ID NO 17
<211> LENGTH: 51
<212> TYPE: DNA
<213> ORGANISM: artificial
<220> FEATURE:
<223> OTHER INFORMATION: Primer

<400> SEQUENCE: 17
ggcggcggcg gctccggtgg tggtggatcc tcagcctctt tctccctggg a    51

<210> SEQ ID NO 18
<211> LENGTH: 51
<212> TYPE: DNA
<213> ORGANISM: artificial
<220> FEATURE:
<223> OTHER INFORMATION: Primer

<400> SEQUENCE: 18
ggcggcggcg gctccggtgg tggtggatcc tcctccctga gtgtgtcagc a    51

<210> SEQ ID NO 19
<211> LENGTH: 51
<212> TYPE: DNA
<213> ORGANISM: artificial
<220> FEATURE:
<223> OTHER INFORMATION: Primer

<400> SEQUENCE: 19
ggcggcggcg gctccggtgg tggtggatcc ctctccctgc ctgtcagtct t    51

<210> SEQ ID NO 20
<211> LENGTH: 51
<212> TYPE: DNA
<213> ORGANISM: artificial
<220> FEATURE:
<223> OTHER INFORMATION: Primer

<400> SEQUENCE: 20
ggcggcggcg gctccggtgg tggtggatcc ctctccctgc ctgtcagtct t    51

<210> SEQ ID NO 21
<211> LENGTH: 44
<212> TYPE: DNA
<213> ORGANISM: artificial
<220> FEATURE:
<223> OTHER INFORMATION: Primer

<400> SEQUENCE: 21
agaacactca ttcctgttga agctcttgac aatgggtgaa gttg    44

<210> SEQ ID NO 22
<211> LENGTH: 54
<212> TYPE: DNA
<213> ORGANISM: artificial
<220> FEATURE:
<223> OTHER INFORMATION: Primer

<400> SEQUENCE: 22
agtgcggccg cagaacactc atcctgttga agctcttgac aatgggtgaa gttg    54

<210> SEQ ID NO 23

<211> LENGTH: 52
<212> TYPE: DNA
<213> ORGANISM: artificial
<220> FEATURE:
<223> OTHER INFORMATION: Primer

<400> SEQUENCE: 23
cgaattccac catggcctgg agccatccgc agttcgagaa gaccggcagc gg         52

<210> SEQ ID NO 24
<211> LENGTH: 48
<212> TYPE: DNA
<213> ORGANISM: artificial
<220> FEATURE:
<223> OTHER INFORMATION: Primer

<400> SEQUENCE: 24
ctatagaagg gtaatacgac tcactatagg gcgaattcca ccatggcc              48

<210> SEQ ID NO 25
<211> LENGTH: 52
<212> TYPE: DNA
<213> ORGANISM: artificial
<220> FEATURE:
<223> OTHER INFORMATION: Primer

<400> SEQUENCE: 25
cgaattccac catggcctgg agccatccgc agttcgagaa gaccggcagc gg         52

<210> SEQ ID NO 26
<211> LENGTH: 54
<212> TYPE: DNA
<213> ORGANISM: artificial
<220> FEATURE:
<223> OTHER INFORMATION: Primer

<400> SEQUENCE: 26
agtgcggccg cagaacactc atcctgttga agctcttgac aatgggtgaa gttg       54

<210> SEQ ID NO 27
<211> LENGTH: 301
<212> TYPE: PRT
<213> ORGANISM: artificial
<220> FEATURE:
<223> OTHER INFORMATION: Polypeptide

<400> SEQUENCE: 27

Met Ala Trp Ser His Pro Gln Phe Glu Lys Thr Gly Ser Gly Asp Val
1               5                   10                  15

Met Leu Val Glu Ser Gly Gly Gly Leu Val Gln Ser Gly Gly Ser Met
                20                  25                  30

Glu Leu Ser Cys Val Ala Ser Gly Ile Thr Phe Gly Asn Tyr Trp Met
            35                  40                  45

Asn Arg Val Arg Gln Ser Pro Glu Lys Gly Leu Glu Trp Val Ala Glu
        50                  55                  60

Ile Arg Leu Lys Ser Asn Asn Tyr Ala Thr His Tyr Val Glu Ser Val
65                  70                  75                  80

Lys Gly Arg Phe Thr Ile Ser Arg Asp Asp Ser Lys Ser Ser Val Tyr
                85                  90                  95

Leu Arg Met Asn Asn Leu Lys Ala Glu Asp Thr Gly Ile Tyr Tyr Cys
            100                 105                 110

Thr Arg His Tyr Tyr Gly Cys Met Asp Tyr Trp Gly Gln Gly Thr Thr
        115                 120                 125

```
Val Thr Val Ser Ser Gly Gly Gly Ser Gly Gly Gly Ser Gly
    130                 135                 140

Gly Gly Gly Ser Gly Gly Gly Ser Leu Ser Leu Pro Val Ser Leu
145                 150                 155                 160

Gly Asp Gln Ala Ser Ile Ser Cys Arg Ser Ser Gln Asn Leu Glu Asp
                165                 170                 175

Ser Asn Gly Lys Thr Phe Leu Asn Trp Tyr Leu Gln Arg Pro Gly Gln
            180                 185                 190

Thr Pro Gln Leu Leu Ile Tyr Arg Val Pro Asn Arg Phe Ser Gly Val
        195                 200                 205

Leu Asp Arg Phe Ser Gly Thr Gly Thr Gly Thr Asp Phe Thr Leu Lys
    210                 215                 220

Ile Ser Arg Val Glu Ala Glu Asp Val Gly Val Tyr Phe Cys Leu Gln
225                 230                 235                 240

Val Thr His Val Pro Pro Thr Phe Gly Gly Gly Thr Lys Leu Glu Leu
                245                 250                 255

Arg Arg Ala Asp Ala Ala Pro Thr Val Ser Ile Phe Pro Pro Ser Ser
            260                 265                 270

Glu Gln Leu Thr Ser Gly Gly Ala Ser Val Val Cys Phe Leu Asn Asn
        275                 280                 285

Phe Thr His Cys Gln Glu Leu Gln Gln Asp Glu Cys Ser
    290                 295                 300

<210> SEQ ID NO 28
<211> LENGTH: 301
<212> TYPE: PRT
<213> ORGANISM: artificial
<220> FEATURE:
<223> OTHER INFORMATION: Polypeptide

<400> SEQUENCE: 28

Met Ala Trp Ser His Pro Gln Phe Glu Lys Thr Gly Ser Gly Asp Val
1               5                   10                  15

Lys Leu Gln Glu Ser Gly Pro Gly Leu Val Lys Pro Ser Gln Ser Leu
            20                  25                  30

Ser Leu Thr Cys Ser Val Thr Gly Tyr Ser Ile Thr Ser Gly Tyr Tyr
        35                  40                  45

Trp Asn Trp Ile Arg Gln Phe Pro Gly Asn Lys Leu Glu Trp Met Gly
    50                  55                  60

Tyr Ile Ser Tyr Asp Gly Ser Asn Asn Tyr Asn Pro Ser Leu Lys Asn
65                  70                  75                  80

Arg Ile Ser Ile Thr Arg Asp Thr Ser Lys Asn Gln Phe Phe Leu Lys
                85                  90                  95

Leu Asn Ser Val Thr Thr Glu Asp Thr Ala Thr Tyr Tyr Cys Ala Arg
            100                 105                 110

Glu Ser Pro Tyr Tyr Gly Ser Ser His Trp Tyr Phe Gly Val Trp Gly
        115                 120                 125

Thr Gly Thr Thr Val Thr Val Ser Ser Gly Gly Gly Ser Gly Gly
    130                 135                 140

Gly Gly Ser Gly Gly Gly Gly Ser Gly Gly Gly Ser Ala Ser Leu
145                 150                 155                 160

Ser Ala Ser Val Gly Glu Thr Val Thr Ile Thr Cys Arg Thr Ser Glu
                165                 170                 175

Asn Ile Tyr Ser Tyr Leu Ala Trp Tyr Gln Gln Lys Gln Gly Lys Ser
            180                 185                 190
```

Pro Gln Leu Leu Val Tyr Asn Ala Lys Thr Leu Ala Glu Gly Val Pro
        195                 200                 205

Ser Arg Phe Ser Gly Ser Gly Ser Gly Thr Gln Phe Ser Leu Lys Ile
210                 215                 220

Asn Ser Leu Gln Pro Glu Asp Phe Gly Ser Tyr Tyr Cys Gln His His
225                 230                 235                 240

Tyr Gly Ile Pro Pro Trp Thr Phe Gly Gly Thr Lys Leu Glu Ile
                245                 250                 255

Lys Arg Ala Asp Ala Ala Pro Thr Val Ser Ile Phe Pro Pro Ser Ser
                260                 265                 270

Glu Gln Leu Thr Ser Gly Gly Ala Ser Val Val Cys Phe Leu Asn Asn
        275                 280                 285

Phe Thr His Cys Gln Glu Leu Gln Gln Asp Glu Cys Ser
        290                 295                 300

<210> SEQ ID NO 29
<211> LENGTH: 299
<212> TYPE: PRT
<213> ORGANISM: artificial
<220> FEATURE:
<223> OTHER INFORMATION: Polypeptide

<400> SEQUENCE: 29

Met Ala Trp Ser His Pro Gln Phe Glu Lys Thr Gly Ser Gly Glu Val
1               5                   10                  15

Gln Leu Val Glu Ser Gly Gly Gly Leu Val Gln Pro Gly Gly Ser Leu
            20                  25                  30

Ser Leu Ser Cys Ala Ala Ser Gly Phe Thr Phe Thr Asp Tyr Tyr Met
        35                  40                  45

Ser Trp Val Arg Gln Pro Pro Gly Lys Ala Leu Glu Trp Leu Gly Phe
50                  55                  60

Ile Arg Asn Lys Ala Asn Gly Tyr Thr Thr Glu Tyr Ser Ala Ser Val
65                  70                  75                  80

Lys Gly Arg Phe Thr Ile Ser Arg Asp Asn Ser Gln Ser Ile Leu Tyr
                85                  90                  95

Leu Gln Met Asn Ala Leu Arg Ala Glu Asp Ser Ala Thr Tyr Tyr Arg
            100                 105                 110

Ala Arg Pro Tyr Tyr Ser Asn Tyr Val Gly Phe Ala Tyr Arg Gly Gln
        115                 120                 125

Gly Thr Leu Val Thr Val Ser Ala Gly Gly Gly Ser Gly Gly Gly
    130                 135                 140

Gly Ser Gly Gly Gly Ser Gly Gly Gly Ser Ala Ser Leu Ser
145                 150                 155                 160

Ala Ser Val Gly Glu Thr Val Thr Ile Thr Cys Arg Ala Ser Glu Asn
                165                 170                 175

Ile Tyr Ser Tyr Leu Ala Trp Tyr Gln Gln Lys Gln Gly Ile Ser Pro
            180                 185                 190

Gln Leu Leu Val Tyr Asn Ala Lys Thr Leu Ala Glu Gly Val Pro Ser
        195                 200                 205

Arg Phe Ser Gly Ser Gly Ser Gly Thr Gln Phe Ser Leu Lys Ile Asn
210                 215                 220

Ser Leu Gln Pro Glu Asp Phe Gly Asn Tyr Tyr Cys Gln His His Tyr
225                 230                 235                 240

Thr Thr Pro Phe Thr Phe Gly Gly Gly Thr Lys Leu Glu Ile Lys Arg
                245                 250                 255

```
Ala Asp Ala Ala Pro Thr Val Ser Ile Phe Pro Ser Ser Glu Gln
            260                 265                 270

Leu Thr Ser Gly Gly Ala Ser Val Val Cys Phe Leu Asn Asn Phe Thr
        275                 280                 285

His Cys Gln Glu Leu Gln Gln Asp Glu Cys Ser
        290                 295

<210> SEQ ID NO 30
<211> LENGTH: 289
<212> TYPE: PRT
<213> ORGANISM: artificial
<220> FEATURE:
<223> OTHER INFORMATION: Polypeptide

<400> SEQUENCE: 30

Met Ala Trp Ser His Pro Gln Phe Glu Lys Thr Gly Ser Gly Gly Ala
1               5                   10                  15

Glu Leu Val Lys Ser Gly Ala Ser Val Lys Leu Ser Cys Thr Ala Ser
            20                  25                  30

Gly Phe Asn Ile Lys Asp Asp Tyr Met His Trp Val Lys Gln Arg Pro
        35                  40                  45

Glu Gln Gly Leu Glu Trp Ile Gly Trp Ile Asp Pro Glu Asn Gly Asp
    50                  55                  60

Thr Glu Tyr Ala Ser Lys Phe Gln Gly Lys Ala Thr Ile Thr Ala Asp
65                  70                  75                  80

Thr Ser Ser Asn Thr Ala Tyr Leu Gln Leu Ser Ser Leu Thr Ser Glu
                85                  90                  95

Asp Thr Ala Val Tyr Tyr Cys Thr Thr Tyr Tyr Gly Ser Ala Trp
            100                 105                 110

Phe Ala Tyr Trp Gly Gln Gly Thr Leu Val Thr Val Ser Ala Gly Gly
        115                 120                 125

Gly Gly Ser Gly Gly Gly Gly Ser Gly Gly Gly Ser Gly Gly Gly Gly
    130                 135                 140

Gly Ser Ala Ser Leu Ser Val Ser Val Gly Glu Thr Val Thr Ile Thr
145                 150                 155                 160

Cys Arg Ala Ser Gly Asn Ile His Asn Tyr Leu Ala Trp Tyr Gln Gln
                165                 170                 175

Lys Gln Gly Lys Ser Pro Gln Leu Leu Val Tyr Asn Ala Lys Thr Leu
            180                 185                 190

Ala Asp Gly Val Pro Ser Arg Phe Ser Gly Ser Gly Ser Gly Thr Gln
        195                 200                 205

Tyr Ser Leu Lys Ile Asn Asn Leu Gln Pro Glu Asp Phe Gly Ser Tyr
    210                 215                 220

Tyr Cys Gln His Phe Trp Ser Thr Pro Tyr Thr Phe Gly Gly Gly Thr
225                 230                 235                 240

Lys Leu Glu Ile Lys Arg Ala Asp Ala Ala Pro Thr Val Ser Ile Phe
                245                 250                 255

Pro Pro Ser Ser Glu Gln Leu Thr Ser Gly Gly Ala Ser Val Val Cys
            260                 265                 270

Phe Leu Asn Asn Phe Thr His Cys Gln Glu Leu Gln Gln Asp Glu Cys
        275                 280                 285

Ser

<210> SEQ ID NO 31
<211> LENGTH: 297
```

```
<212> TYPE: PRT
<213> ORGANISM: artificial
<220> FEATURE:
<223> OTHER INFORMATION: Polypeptide

<400> SEQUENCE: 31

Met Ala Trp Ser His Pro Gln Phe Glu Lys Thr Gly Ser Gly Gln Val
1               5                   10                  15

Gln Leu Gln Gln Ser Gly Ala Glu Leu Val Lys Pro Gly Ala Ser Val
            20                  25                  30

Lys Ser Ser Cys Thr Ala Thr Gly Phe Asn Ile Lys Asp Tyr Tyr Ile
        35                  40                  45

His Trp Val Lys Gln Arg Thr Glu Gln Gly Leu Glu Trp Ile Gly Arg
    50                  55                  60

Ile Asp Pro Glu Asp Gly Glu Thr Lys Tyr Ala Pro Lys Phe Gln Gly
65                  70                  75                  80

Lys Ala Thr Ile Thr Ala Asp Ile Ser Pro Asn Thr Ala Tyr Leu Gln
                85                  90                  95

Pro Ser Ser Leu Thr Ser Glu Asp Thr Ala Val Tyr Tyr Cys Thr Arg
            100                 105                 110

Gly Gly Tyr Tyr Gly Pro Trp Tyr Phe Asp Val Trp Gly Thr Gly Thr
        115                 120                 125

Thr Val Thr Val Ser Ser Gly Gly Gly Ser Gly Gly Gly Gly Gly Ser
130                 135                 140

Gly Gly Gly Gly Ser Gly Gly Gly Ser Ala Ser Leu Ser Val Ser
145                 150                 155                 160

Val Gly Glu Thr Val Thr Ile Thr Cys Arg Ala Ser Glu Asn Ile Tyr
                165                 170                 175

Ser Tyr Leu Ala Trp Tyr Gln Gln Lys Gln Gly Lys Ser Pro Gln Leu
            180                 185                 190

Leu Val Tyr Asn Ala Lys Thr Leu Ala Glu Gly Val Pro Ser Arg Phe
        195                 200                 205

Ser Gly Ser Gly Ser Gly Thr Gln Phe Ser Leu Lys Ile Asn Asn Leu
    210                 215                 220

Gln Pro Glu Asp Phe Gly Ser Tyr Tyr Cys Gln Arg His Tyr Asp Thr
225                 230                 235                 240

Pro Tyr Thr Phe Gly Gly Gly Thr Lys Leu Glu Ile Lys Arg Ala Asp
                245                 250                 255

Ala Ala Pro Thr Val Ser Ile Phe Pro Pro Ser Ser Glu Gln Leu Thr
            260                 265                 270

Ser Gly Gly Ala Ser Val Val Cys Phe Leu Asn Asn Phe Thr His Cys
        275                 280                 285

Gln Glu Leu Gln Gln Asp Glu Cys Ser
    290                 295

<210> SEQ ID NO 32
<211> LENGTH: 308
<212> TYPE: PRT
<213> ORGANISM: artificial
<220> FEATURE:
<223> OTHER INFORMATION: Polypeptide

<400> SEQUENCE: 32

Met Ala Trp Ser His Pro Gln Phe Glu Lys Thr Gly Ser Gly Gln Val
1               5                   10                  15

Gln Leu Gln Gln Ser Gly Ala Glu Leu Val Lys Pro Gly Ala Ser Val
            20                  25                  30
```

```
Lys Leu Ser Cys Lys Ala Ser Gly Tyr Thr Phe Thr Glu Tyr Thr Ile
            35                  40                  45
His Trp Val Lys Gln Arg Ser Gly Gln Gly Leu Glu Trp Ile Gly Trp
        50                  55                  60
Phe Tyr Pro Gly Ser Gly Ser Ile Lys Tyr Asp Glu Lys Phe Lys Asp
65                  70                  75                  80
Lys Ala Thr Leu Thr Ala Asp Lys Ser Ser Thr Val Tyr Met Glu
            85                  90                  95
Leu Ser Arg Leu Thr Ser Glu Asp Ser Ala Val Tyr Phe Cys Ala Arg
            100                 105                 110
His Glu Pro Tyr Tyr Gly Ser Ser Tyr Glu Gly Pro Phe Asp Tyr
            115                 120                 125
Trp Gly Gln Gly Thr Thr Leu Thr Val Ser Ser Gly Gly Gly Ser
        130                 135                 140
Gly Gly Gly Gly Ser Gly Gly Gly Ser Gly Gly Gly Ser Ser
145                 150                 155                 160
Pro Leu Ser Val Ser Ala Gly Glu Lys Val Thr Met Ser Cys Lys Ser
            165                 170                 175
Ser Gln Ser Leu Leu Asn Ser Gly Asn Gln Lys Asn Tyr Leu Ala Trp
            180                 185                 190
Tyr Gln Gln Lys Pro Gly Gln Pro Pro Lys Leu Leu Ile Tyr Gly Ala
            195                 200                 205
Ser Thr Arg Glu Ser Gly Val Pro Asp Arg Phe Thr Gly Ser Gly Ser
            210                 215                 220
Gly Thr Asp Phe Thr Leu Thr Ile Ser Ser Val Gln Ala Glu Asp Leu
225                 230                 235                 240
Ala Val Tyr Tyr Cys Gln Asn Asp His Ser Tyr Pro Leu Thr Phe Gly
            245                 250                 255
Ala Gly Thr Lys Leu Glu Leu Lys Arg Ala Asp Ala Ala Pro Thr Val
            260                 265                 270
Ser Ile Phe Pro Pro Ser Ser Glu Gln Leu Thr Ser Gly Gly Ala Ser
            275                 280                 285
Val Val Cys Phe Leu Asn Asn Phe Thr His Cys Gln Glu Leu Gln Gln
            290                 295                 300
Asp Glu Cys Ser
305

<210> SEQ ID NO 33
<211> LENGTH: 301
<212> TYPE: PRT
<213> ORGANISM: artificial
<220> FEATURE:
<223> OTHER INFORMATION: Polypeptide

<400> SEQUENCE: 33

Met Ala Trp Ser His Pro Gln Phe Glu Lys Thr Gly Ser Gly Glu Val
1               5                   10                  15
Gln Leu Gln Gln Ser Gly Ala Glu Leu Met Lys Pro Gly Ala Ser Val
            20                  25                  30
Lys Leu Ser Cys Lys Ala Thr Ser Tyr Thr Phe Thr Gly Tyr Trp Ile
            35                  40                  45
Glu Trp Val Lys Gln Arg Pro Gly Arg Gly Leu Glu Trp Ile Gly Glu
        50                  55                  60
Ile Leu Pro Gly Ser Gly Ser Thr Asn Tyr Asn Glu Lys Phe Lys Gly
65                  70                  75                  80
```

Lys Ala Thr Phe Thr Ala Asp Thr Ser Ser Asn Thr Ala Tyr Met Gln
                85                  90                  95

Leu Ser Ser Pro Thr Thr Glu Asp Ser Ala Ile Tyr Tyr Cys Ala Arg
            100                 105                 110

Asp Tyr Tyr Asp Trp Tyr Phe Asp Val Trp Gly Thr Gly Thr Thr Val
        115                 120                 125

Thr Val Ser Ser Gly Gly Gly Gly Ser Gly Gly Gly Gly Ser Gly Gly
    130                 135                 140

Gly Gly Ser Gly Gly Gly Ser Ser Leu Ser Val Ser Ala Gly
145                 150                 155                 160

Glu Lys Val Thr Met Ser Cys Lys Ser Gln Ser Leu Leu Asn Ser
                165                 170                 175

Gly Asn Gln Lys Asn Tyr Leu Ala Trp Tyr Gln Gln Lys Pro Gly Gln
            180                 185                 190

Pro Pro Lys Leu Leu Ile Tyr Gly Ala Ser Thr Arg Glu Ser Gly Val
        195                 200                 205

Pro Asp Arg Leu Thr Gly Ser Gly Ser Gly Thr Asp Phe Thr Leu Thr
    210                 215                 220

Ile Ser Ser Val Gln Ala Glu Asp Leu Ala Val Tyr Tyr Cys Gln Asn
225                 230                 235                 240

Asp His Ser Tyr Pro Trp Thr Phe Gly Gly Gly Thr Lys Leu Glu Ile
                245                 250                 255

Lys Arg Ala Asp Ala Ala Pro Thr Val Ser Ile Phe Pro Pro Ser Ser
            260                 265                 270

Glu Gln Leu Thr Ser Gly Gly Ala Ser Val Val Cys Phe Leu Asn Asn
        275                 280                 285

Phe Thr His Cys Gln Glu Leu Gln Gln Asp Glu Cys Ser
    290                 295                 300

<210> SEQ ID NO 34
<211> LENGTH: 298
<212> TYPE: PRT
<213> ORGANISM: artificial
<220> FEATURE:
<223> OTHER INFORMATION: Polypeptide

<400> SEQUENCE: 34

Met Ala Trp Ser His Pro Gln Phe Glu Lys Thr Gly Ser Gly Gly Ala
1               5                   10                  15

Glu Leu Val Arg Ser Gly Ala Ser Val Lys Leu Ser Cys Thr Ala Ser
            20                  25                  30

Gly Phe Asn Ile Lys Asp Asp Tyr Met His Trp Val Lys Gln Arg Pro
        35                  40                  45

Glu Gln Gly Leu Lys Trp Ile Gly Trp Ile Asp Pro Glu Asn Gly Asp
    50                  55                  60

Thr Glu Tyr Ala Ser Lys Leu Gln Gly Lys Ala Thr Ile Thr Ala Asp
65                  70                  75                  80

Thr Ser Ser Asn Thr Ala Tyr Leu Gln Leu Ser Ser Leu Thr Ser Glu
                85                  90                  95

Asp Thr Ala Val Tyr Tyr Cys Ala Arg Pro Ile Tyr Tyr Gly Ser
            100                 105                 110

Ser His Trp Tyr Phe Asp Val Trp Gly Thr Gly Thr Thr Val Thr Val
        115                 120                 125

Ser Ser Gly Gly Gly Gly Ser Gly Gly Gly Gly Ser Gly Gly Gly Gly
    130                 135                 140

Ser Gly Gly Gly Gly Ser Leu Ser Leu Pro Val Ser Leu Gly Asp Gln
145                 150                 155                 160

Ala Ser Ile Ser Cys Arg Ser Ser Gln Ser Leu Val His Ser Asn Gly
            165                 170                 175

Asn Thr Tyr Leu His Trp Tyr Leu Gln Lys Pro Gly Gln Ser Pro Lys
        180                 185                 190

Leu Leu Ile Tyr Lys Val Ser Asn Arg Phe Ser Gly Val Pro Asp Arg
            195                 200                 205

Phe Ser Gly Ser Gly Ser Gly Thr Asp Phe Thr Leu Lys Ile Ser Arg
    210                 215                 220

Val Glu Ala Glu Asp Leu Gly Val Tyr Phe Cys Ser Gln Ser Thr His
225                 230                 235                 240

Val Pro Trp Thr Phe Gly Gly Gly Thr Lys Leu Glu Val Lys Arg Ala
                245                 250                 255

Asp Ala Ala Pro Thr Val Ser Ile Phe Pro Pro Ser Ser Glu Gln Leu
            260                 265                 270

Thr Ser Gly Gly Ala Ser Val Val Cys Phe Leu Asn Asn Phe Thr His
        275                 280                 285

Cys Gln Glu Leu Gln Gln Asp Glu Cys Ser
    290                 295

<210> SEQ ID NO 35
<211> LENGTH: 305
<212> TYPE: PRT
<213> ORGANISM: artificial
<220> FEATURE:
<223> OTHER INFORMATION: Polypeptide

<400> SEQUENCE: 35

Met Ala Trp Ser His Pro Gln Phe Glu Lys Thr Gly Ser Gly Gln Val
1               5                   10                  15

Gln Leu Gln Gln Pro Gly Ala Glu Leu Val Lys Pro Gly Ala Ser Val
            20                  25                  30

Lys Leu Ser Cys Lys Ala Ser Gly Tyr Thr Phe Thr Ser Tyr Trp Met
        35                  40                  45

His Trp Val Lys Gln Arg Pro Gly Arg Gly Leu Glu Trp Ile Gly Arg
    50                  55                  60

Ile Asp Pro Asn Ser Gly Gly Thr Lys Tyr Asn Glu Lys Phe Lys Ser
65                  70                  75                  80

Lys Ala Thr Leu Thr Val Asp Lys Pro Ser Ser Thr Ala Tyr Met Gln
                85                  90                  95

Leu Ser Ser Leu Thr Ser Glu Asp Ser Ala Val Tyr Tyr Cys Ala Arg
            100                 105                 110

Thr Gly Tyr Tyr Gly Ser Ser Trp Tyr Phe Asp Val Trp Gly Thr Gly
        115                 120                 125

Thr Thr Val Thr Val Ser Ser Gly Gly Gly Ser Gly Gly Gly Gly
    130                 135                 140

Ser Gly Gly Gly Gly Ser Gly Gly Gly Gly Ser Leu Ser Leu Pro Val
145                 150                 155                 160

Ser Leu Gly Asp Gln Ala Ser Ile Ser Cys Arg Ser Ser Gln Ser Ile
                165                 170                 175

Val His Ser Asn Gly Asn Thr Tyr Leu Glu Trp Tyr Leu Gln Lys Pro
            180                 185                 190

Gly Gln Ser Pro Lys Leu Leu Ile Tyr Lys Val Ser Asn Arg Phe Ser
        195                 200                 205

```
Gly Val Pro Asp Arg Phe Ser Gly Ser Gly Ser Gly Thr Asp Phe Thr
        210                 215                 220

Leu Lys Ile Ser Arg Val Glu Ala Glu Asp Leu Gly Val Tyr Tyr Cys
225                 230                 235                 240

Phe Gln Gly Ser His Val Pro Pro Leu Tyr Thr Phe Gly Gly Gly Thr
                245                 250                 255

Lys Leu Glu Ile Lys Arg Ala Asp Ala Ala Pro Thr Val Ser Ile Phe
            260                 265                 270

Pro Pro Ser Ser Glu Gln Leu Thr Ser Gly Gly Ala Ser Val Val Cys
        275                 280                 285

Phe Leu Asn Asn Phe Thr His Cys Gln Glu Leu Gln Gln Asp Glu Cys
290                 295                 300

Ser
305

<210> SEQ ID NO 36
<211> LENGTH: 299
<212> TYPE: PRT
<213> ORGANISM: artificial
<220> FEATURE:
<223> OTHER INFORMATION: Polypeptide

<400> SEQUENCE: 36

Met Ala Trp Ser His Pro Gln Phe Glu Lys Thr Gly Ser Gly Gln Val
1               5                   10                  15

Gln Leu Gln Gln Pro Gly Thr Glu Leu Val Lys Pro Gly Ala Ser Val
            20                  25                  30

Lys Leu Ser Cys Lys Ala Ser Gly Tyr Thr Phe Thr Ser Tyr Trp Met
        35                  40                  45

His Trp Val Lys Gln Arg Pro Gly Gln Gly Leu Glu Trp Ile Gly Asn
    50                  55                  60

Thr Asn Pro Ser Asn Gly Gly Thr Asn Tyr Asn Glu Lys Phe Lys Ser
65                  70                  75                  80

Lys Ala Thr Leu Thr Val Asp Lys Ser Ser Asn Thr Ala Tyr Met Gln
                85                  90                  95

Leu Ser Ser Leu Thr Ser Glu Asp Ser Ala Val Tyr Tyr Cys Ala Arg
            100                 105                 110

Ser Val Ser Gly Asn Phe Ala Tyr Trp Gly Gln Gly Thr Leu Val Thr
        115                 120                 125

Val Ser Ala Gly Gly Gly Gly Ser Gly Gly Gly Gly Ser Gly Gly Gly
    130                 135                 140

Gly Ser Gly Gly Gly Gly Ser Leu Ser Leu Pro Val Ser Leu Gly Asp
145                 150                 155                 160

Gln Ala Ser Ile Ser Cys Arg Ser Ser Gln Ser Leu Val His Ser Asn
                165                 170                 175

Gly Asn Thr Tyr Leu His Trp Tyr Leu Gln Lys Pro Gly Gln Ser Pro
            180                 185                 190

Lys Leu Leu Ile Tyr Lys Val Ser Asn Arg Phe Ser Gly Val Pro Asp
        195                 200                 205

Arg Phe Ser Gly Ser Gly Ser Gly Thr Asp Phe Thr Leu Lys Ile Ser
    210                 215                 220

Arg Val Glu Ala Glu Asp Leu Gly Val Tyr Phe Cys Ser Gln Ser Thr
225                 230                 235                 240

His Val Pro Trp Thr Phe Gly Gly Gly Thr Lys Leu Glu Ile Lys Arg
                245                 250                 255
```

```
Ala Asp Ala Ala Pro Thr Val Ser Ile Phe Pro Pro Ser Ser Glu Gln
            260                 265                 270

Leu Thr Ser Gly Gly Ala Ser Val Val Cys Phe Leu Asn Asn Phe Thr
        275                 280                 285

His Cys Gln Glu Leu Gln Gln Asp Glu Cys Ser
    290                 295
```